US011666290B2

(12) United States Patent
Wilson et al.

(10) Patent No.: US 11,666,290 B2
(45) Date of Patent: *Jun. 6, 2023

(54) RADIOABSORBENT ASSEMBLIES

(71) Applicant: Egg Medical, Inc., Maple Grove, MN (US)

(72) Inventors: Robert F. Wilson, Maple Grove, MN (US); Uma S. Valeti, Maple Grove, MN (US); John P. Gainor, Maple Grove, MN (US)

(73) Assignee: Egg Medical, Inc., Arden Hills, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/402,260

(22) Filed: Aug. 13, 2021

(65) Prior Publication Data

US 2021/0369218 A1 Dec. 2, 2021

Related U.S. Application Data

(63) Continuation of application No. 16/559,500, filed on Sep. 3, 2019, now Pat. No. 11,191,495, which is a continuation of application No. 16/005,339, filed on Jun. 11, 2018, now Pat. No. 10,441,231, which is a continuation of application No. 15/291,941, filed on Oct. 12, 2016, now Pat. No. 10,016,172.

(60) Provisional application No. 62/240,409, filed on Oct. 12, 2015.

(51) Int. Cl.
*A61B 6/10* (2006.01)
*G21F 1/12* (2006.01)
*G21F 3/00* (2006.01)
*A61B 6/00* (2006.01)

(52) U.S. Cl.
CPC ............... *A61B 6/107* (2013.01); *G21F 1/12* (2013.01); *G21F 3/00* (2013.01); *A61B 6/4441* (2013.01); *A61B 6/487* (2013.01)

(58) Field of Classification Search
CPC ....... A61B 6/107; A61B 6/4441; A61B 6/487; G21F 1/12; G21F 3/00
See application file for complete search history.

(56) References Cited

U.S. PATENT DOCUMENTS

| 6,448,571 | B1 | 9/2002 | Goldstein |
| 6,471,167 | B1 | 10/2002 | Myers et al. |
| 6,653,648 | B2 | 11/2003 | Goldstein |

(Continued)

FOREIGN PATENT DOCUMENTS

| GB | 1051979 A1 | 12/1966 |
| WO | WO 2014/078553 A1 | 5/2014 |

OTHER PUBLICATIONS

Japan Patent Office, Office Action dated Jun. 18, 2020 in Japanese Patent Application No. 2018-518980 filed Apr. 12, 2018 (with English translation), 10 pages.

(Continued)

*Primary Examiner* — Nicole M Ippolito
*Assistant Examiner* — Hanway Chang
(74) *Attorney, Agent, or Firm* — Inskeep IP Group, Inc.

(57) ABSTRACT

A system of shields designed to provide substantially greater protection, head to toe, against radiation exposure to health care workers in a hospital room during procedures which require real-time imaging. The shields are placed around the patient and the x-ray table and provide protection even when the x-ray tube is moved to various angles around the patient.

20 Claims, 21 Drawing Sheets

(56) References Cited

U.S. PATENT DOCUMENTS

| | | |
|---|---|---|
| 7,057,194 B2 | 6/2006 | Goldstein |
| 7,391,042 B2 | 6/2008 | Goldstein |
| 7,638,784 B2 | 12/2009 | Fox et al. |
| 8,716,687 B2 | 5/2014 | Goldstein et al. |
| 9,655,571 B2 | 5/2017 | Hunt |
| 10,441,231 B2 | 10/2019 | Wilson et al. |
| 2006/0124871 A1 | 6/2006 | Ballsieper |
| 2006/0156472 A1 | 7/2006 | Ansel |
| 2011/0095209 A1 | 4/2011 | Cadwalader et al. |
| 2012/0132217 A1 | 5/2012 | Rees |
| 2014/0029720 A1 | 1/2014 | Osherov et al. |
| 2014/0151584 A1 | 6/2014 | Khandkar et al. |
| 2018/0164425 A1 | 6/2018 | Berge et al. |

OTHER PUBLICATIONS

European Patent Office, Supplementary European Search Report dated Oct. 25, 2018 in European Patent Application No. 16882231, 7 pages.
WIPO, U.S. International Search Authority, International Search Report and Written Opinion dated Aug. 29, 2017 in International Patent Application No. PCT/US2016/056664, 9 pages.
European Patent Office, Extended European Search Report dated Dec. 12, 2022 in European Patent Application No. 22168054.9, 8 pages.

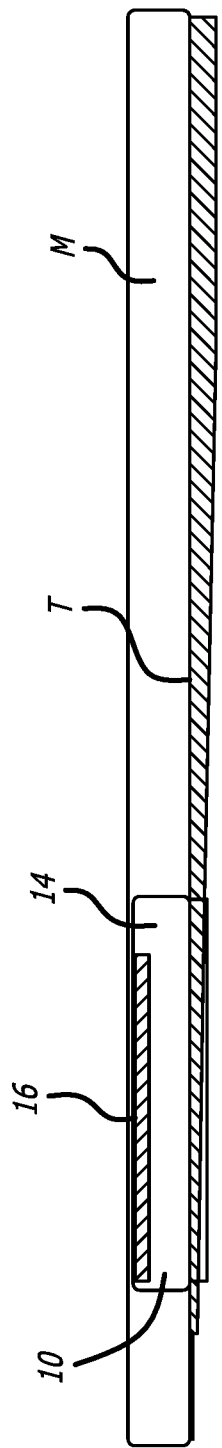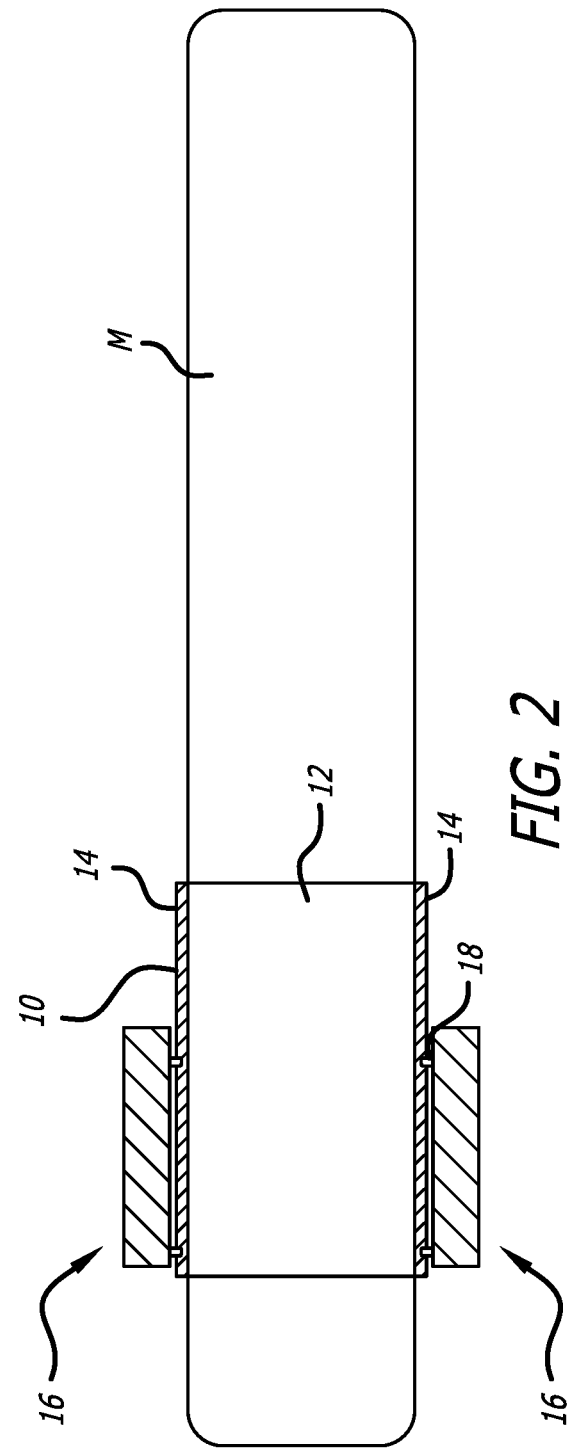

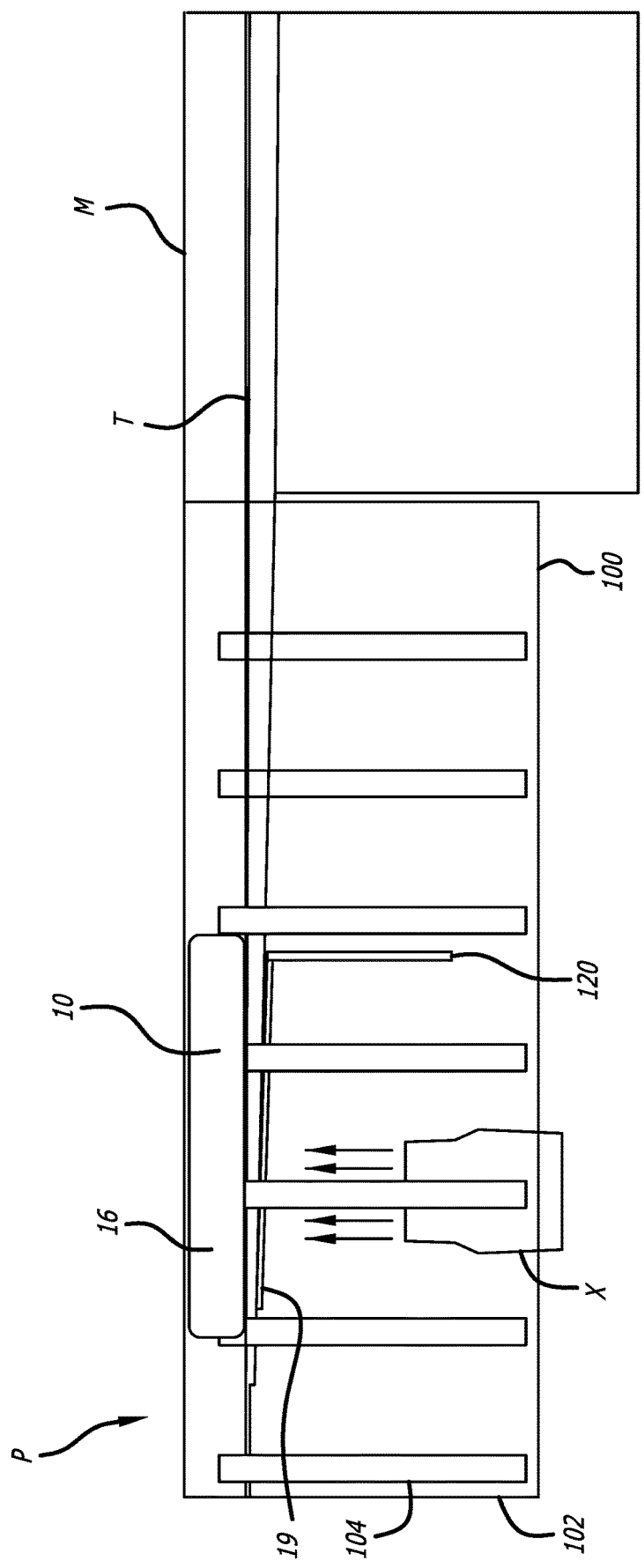

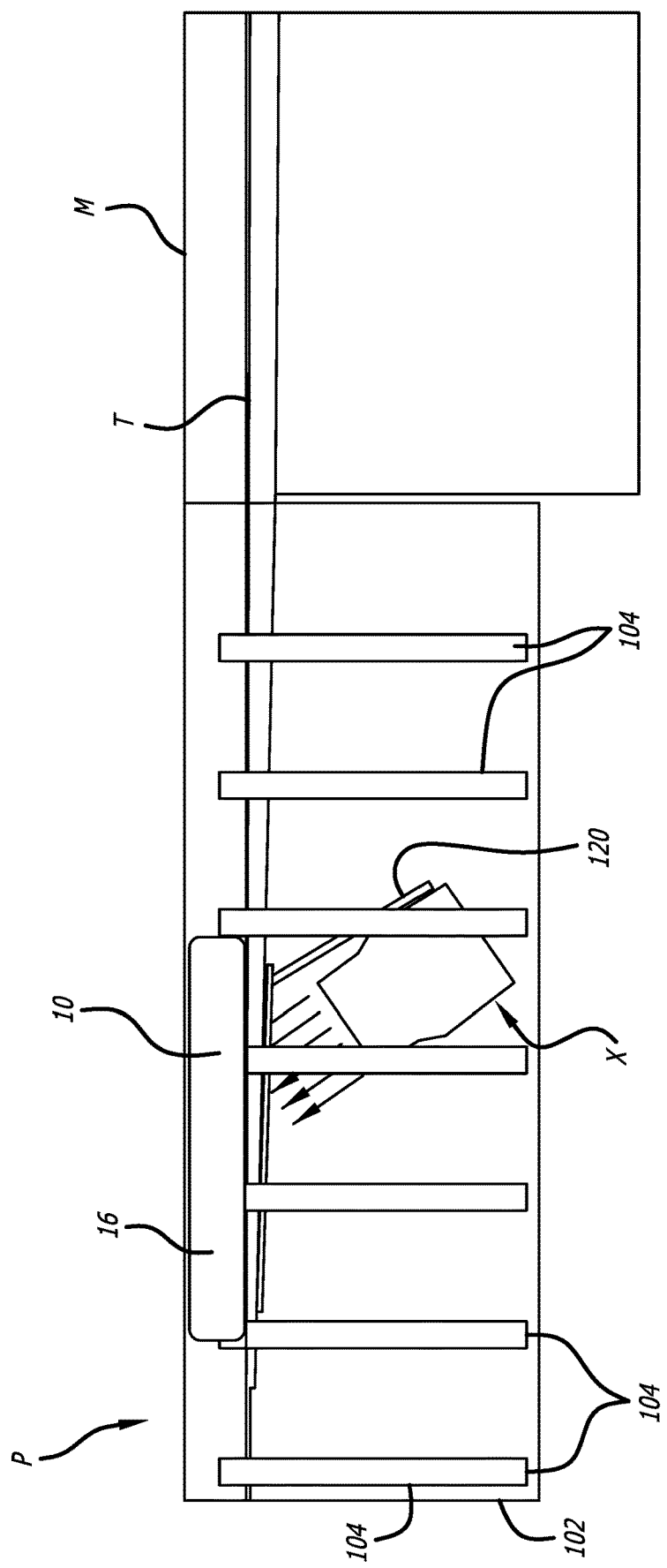

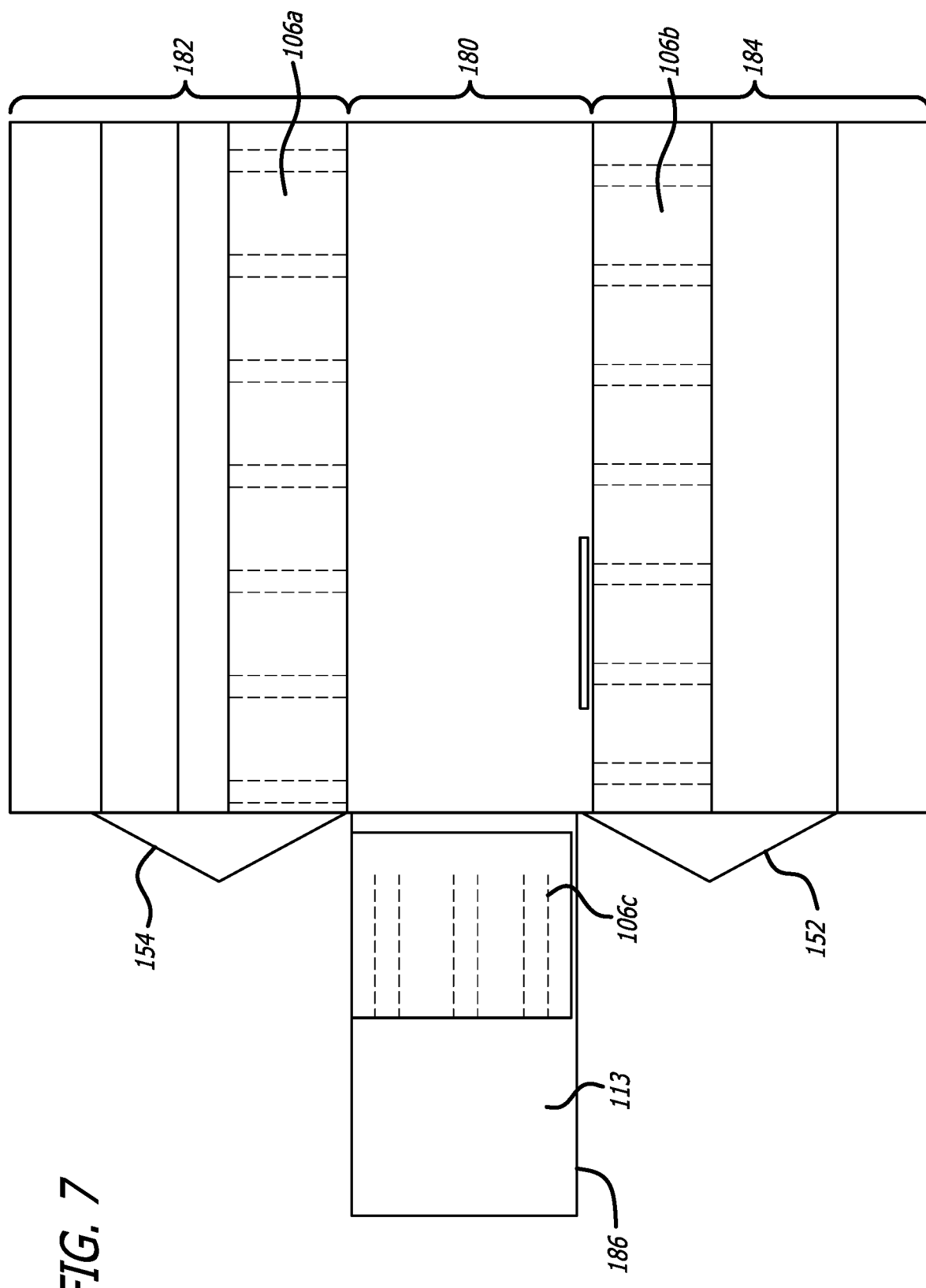

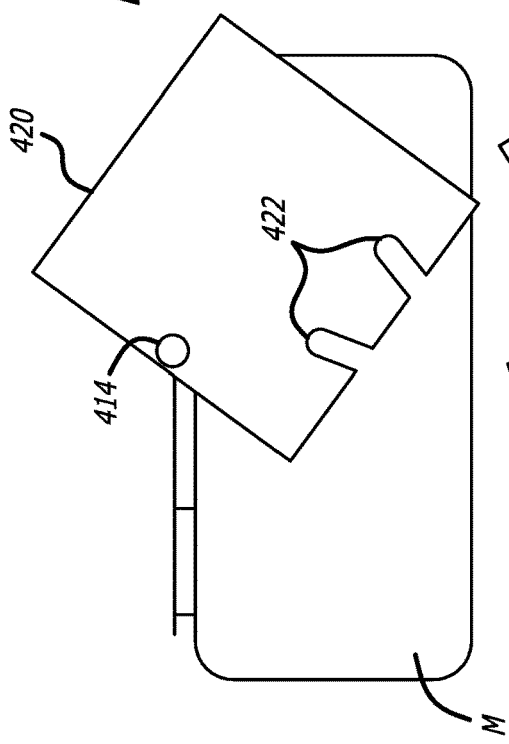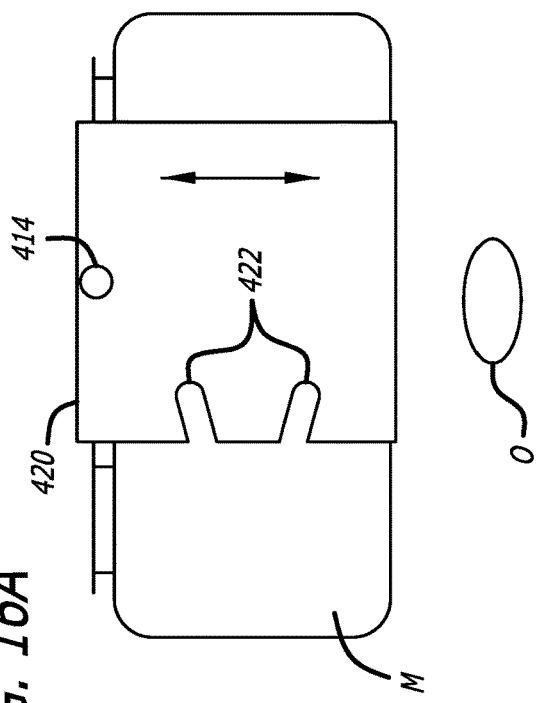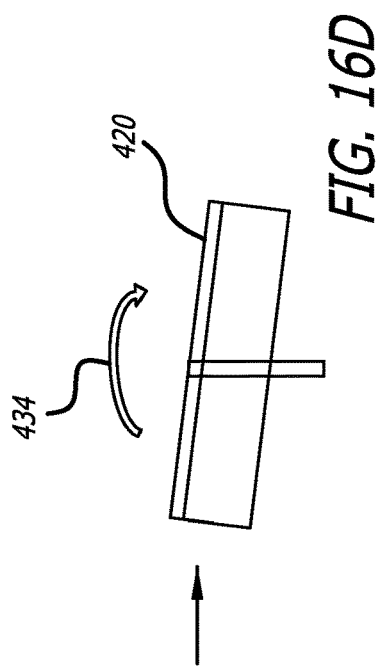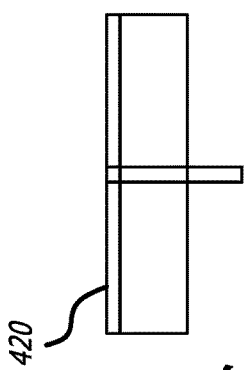

Test Positions

1. Imaging cardiologist
2. Right heart catheterization cardiologist
3. Heart biopsy cardiologist
4. Femoral or radial access angiography cardiologist
5. Assistant
6. Nurse

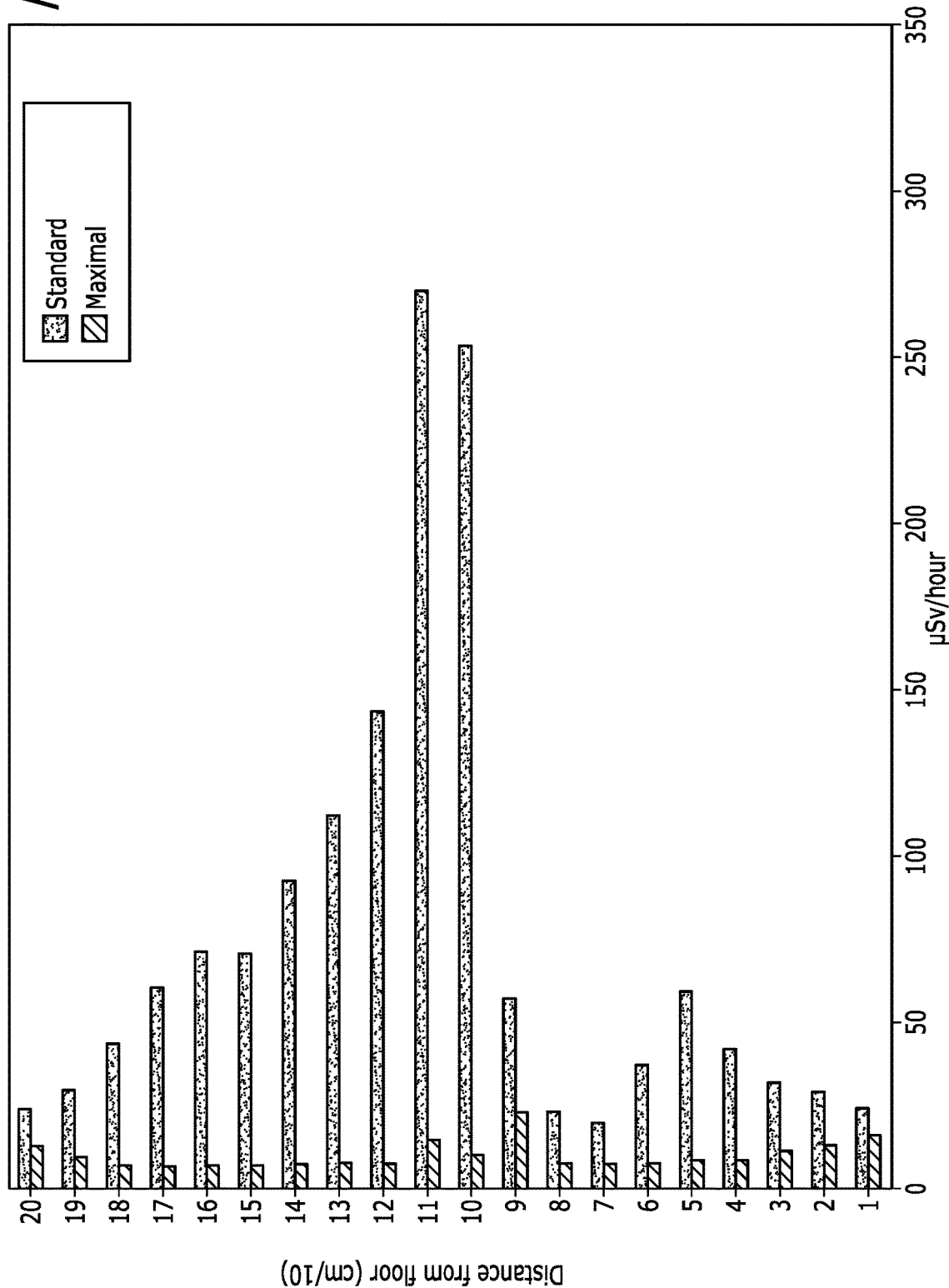

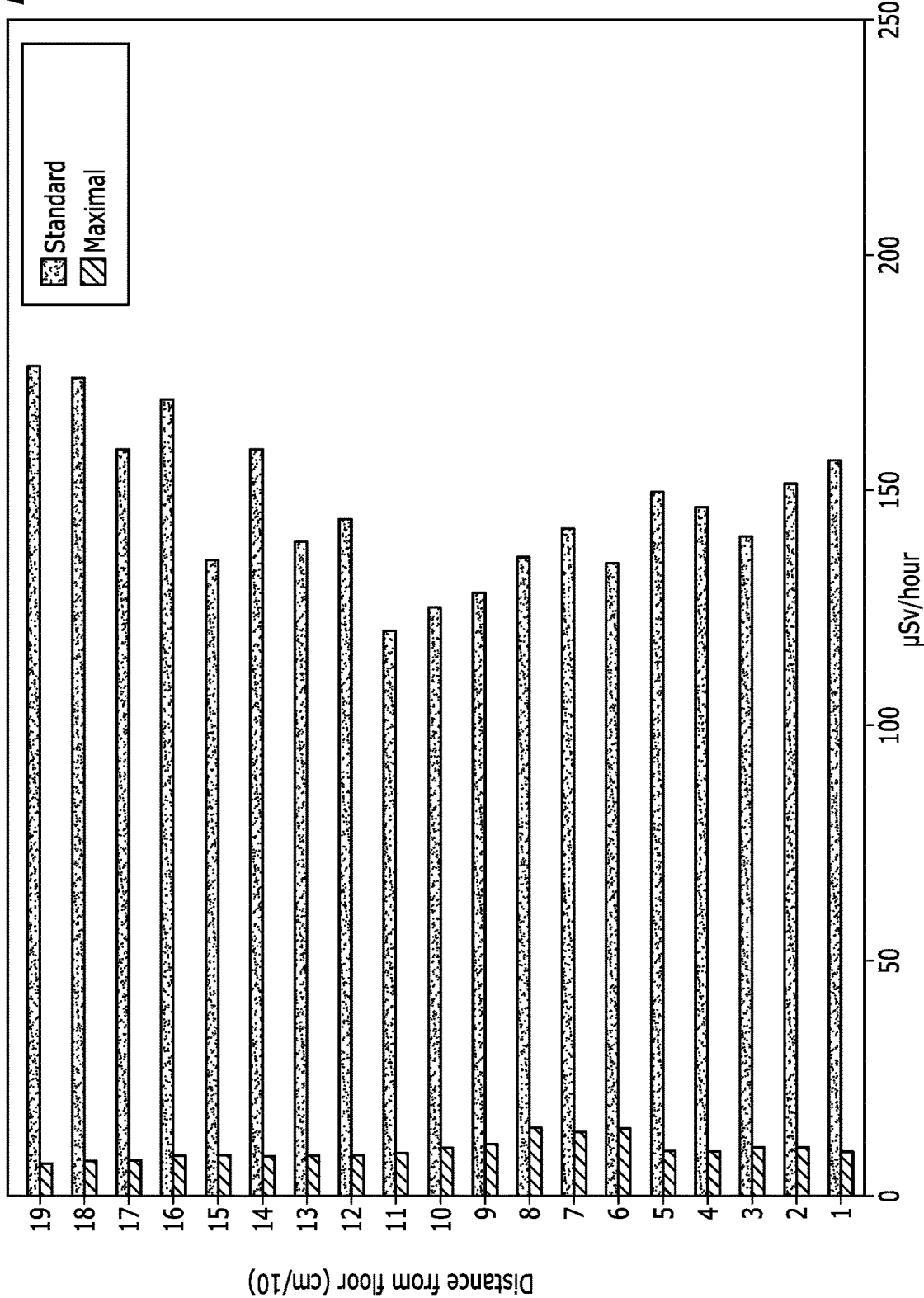

RADIOABSORBENT ASSEMBLIES

RELATED APPLICATIONS

This application is a continuation of U.S. patent application Ser. No. 16/559,500 filed Sep. 3, 2019 entitled *Radioabsorbent Assemblies*, which is a continuation of U.S. patent application Ser. No. 16/005,339 filed Jun. 11, 2018 entitled *Radioabsorbent Assemblies* (now U.S. patent Ser. No. 10/441,231 issued Oct. 15, 2019), which is a continuation of U.S. patent application Ser. No. 15/291,941 filed Oct. 12, 2016 entitled *Radioabsorbent Assemblies* (now U.S. Pat. No. 10,016,172 issued Jul. 10, 2018), which claims benefit of and priority to U.S. Provisional Application Ser. No. 62/240,409 filed Oct. 12, 2015 entitled *Radioabsorbent Assemblies*, all of which are hereby incorporated herein by reference in their entireties.

FIELD OF THE INVENTION

The present invention pertains to various embodiments of radiation shields to protect physicians and other health care workers present during procedures requiring real-time X-ray imaging.

BACKGROUND OF THE INVENTION

Radiation exposure during medical procedures requiring x-rays or other ionizing radiation is a major health concern for health care workers (HCW). Procedures requiring real-time imaging, such as percutaneous procedures, involve a patient on a table with an x-ray device mounted on a C-arm, known as an x-ray gantry. The radiation is emitted from a "tube" on the bottom of the C-arm and is directed upward through the bottom of the table and the patient. The physician and other attending HCWs are typically standing next to the table attending the patient and are subject to the radiation.

Most of the radiation exposure to the HCWs emanate from x-ray photons that are reflected off of the patient's bones and other structures during the procedures. More specifically, the exposure to the HCWs from their waists down result from x-rays coming directly from the tube, as well as reflecting off of the table structure and the bones of the patient. Exposure to the HCWs from their waists up result from X-rays reflecting off of the bones of the patient and structures above the patient.

Most are composed of an x-ray blocking material in the form of a hard, planar shield. These are attached to the ceiling or x-ray table. Some are flexible and some are clear. They are cumbersome, do not conform to the patient's anatomy (reducing effectiveness in blocking x-rays), do not facilitate surgical access to the body, and do not provide storage for tools or lighting.

Additionally, these shields are heavy and often get in the way of adequate fluoroscopic visualization of the patient or key areas of the patient that require easy access or monitoring. The HCW has to move these heavy shields manually and also conform their bodies to visualize around the impediments caused by the existing devices. This is a major cause for musculoskeletal morbidity of the HCW resulting in chronic neck, back injuries. Consequently, it is common for the HCW to sacrifice radiation protection for better visualization as well as better ergonomics by moving the current shields out of the way or positioning them in a markedly sub-optimal protection position. Finally, it is not uncommon that the HCW forgets to move the shields for adequate protection.

Other x-ray blocking shields have consisted of draping x-ray absorbing material (DXAM) over the patient during procedures. Because these draped materials lay on the patient, they need to be covered with sterile material or be disposed of after every use. This is cumbersome and, as a result, most of the draped material is made as a disposable item (disposable drape and x-ray barrier inside), increasing cost and toxic waste. Moreover, the draped polymer is heavy and uncomfortable for the patient because the patient supports the weight. Additionally, because the DXAM is positioned under the sterile drape that covers the patient, it is difficult to remove during the procedure should an emergency arise that requires more x-ray visualization.

Another problem in protecting personnel from scatter x-ray exposure during medical procedures is that, when the x-ray source is below the patient, the x-ray is scattered off of the patient toward the floor. As a result, the legs and feet of personnel are heavily exposed to ionizing radiation. In addition, the x-ray tube housing can often leak substantial x-radiation, often of high energy. This also increases personnel exposure to high energy ionizing radiation.

Current shielding for "below-the-table" radiation consists primarily of a radiation blocking barrier (called the table skirt) that hangs from the table. Since the table height is varied during the procedure, there is often a gap between the floor and the barrier. Additionally, these table skirts are usually hung on a lever arm from the foot end of the x-ray table. They do not cover the gap between the table and the floor from the mid abdomen to the head. As a result, personnel in the room stationed at the patient's head or side receive substantial radiation exposure. This is a particular risk for physicians performing procedures that require manipulation of catheters near the patient's head (such as subclavian or jugular vein access, subclavian artery access, or transesophageal ultrasound imaging).

OBJECTS AND SUMMARY OF THE INVENTION

There is thus a need for a shielding system that allows a HCW access to a patient while protecting the HCW from radiation. The invention described herein provides several embodiments directed toward providing protection both below and above the waist as well as protecting HCWs located in various positions relative to the patient.

The system of the invention includes a suite of shields and accessories that provide protection and convenience to HCWs working in x-ray imaging environments. The suite includes several components that extend from, or are attachable to a sled that carries a mattress and is attachable to an x-ray table. The radiation protection suite of the invention includes table shields, which extend below the table and protect the HCWs from the waist down. The suite also includes vertical flags that extend upwards and across the body of the patient. The suite further includes body shields, which extend upward from the sled and run along the sides of the patient. Wing shields are also included, which also extend upward along the sides of the patient. The wing shields are generally higher and more rigid than the body shields, providing more protection in high dosage areas. Finally, a tray is provided that extends horizontally across the body of the patient and provides both shielding as well as a work surface for the HCWs.

Mini Sled

In one aspect of the invention a "mini-sled" is provided. In particular, the shielding drape is connected actively or passively to a sled that holds a mattress on which the patient lies during the medical procedure. The sled has a bottom that lays on the x-ray table and two perpendicular sides, typically about 1-4 inches in height. A mattress lies within the U-shaped cavity of the sled. The sled can be the entire length of the mattress or shorter length. The table shield drape is positioned over the sled passively (by gravity) or actively attached. The active attachment can be reversible (such as by a zipper or hook and eye mechanism) or non-reversible (such as with a bonding agent).

In one embodiment, attachment points for arm boards, shields or other devices protrude from the sled through the tray shield and attach to such devices. In the preferred embodiment, the arm boards rotate on the attachments to the sled, such that they can be flush to the sides of the sled in the down position, parallel to the x-ray table in the neutral position, or vertical above the sled in the up position. This allows stowage when transferring a patient off of the bed (down position), support of the patients arms during the procedure (neutral position), or clearance of the x-ray gantry when a lateral view is desired (up position). In addition, in the preferred embodiment, the arm boards pivot outward from the head-ward attachment, allowing the arm to abduct. This feature is important for optimal arm positioning for radial arterial catheterization.

Table Shields

One aspect provided by the invention is a shielding drape, or "table shield" that extends down from the top of the sled toward the floor. Through experimentation it has been found that an HCW attending tableside to a patient undergoing imaging absorbs significant levels of radiation in their legs and feet that have been historically ignored. Measurements of radiation exposure during use prove that assumptions that the tube housing of the imaging device protects the HCW from radiation exposure are wrong.

A table shield of the invention virtually eliminates below-the-table scatter radiation exposure to personnel. In addition, attachments markedly reduce scatter radiation from the patient's head, chest, abdomen, and pelvic area.

A table shield of the invention is constructed of a flexible radioabsorbent material such as vinyl fabric, that covers the patient procedure mat and table, where the sides of the material contain radiation blocking material sandwiched within the vinyl material In one embodiment, the table shield has two or more layers of fabric or other material in the portion that lays across the x-ray table or mattress situated on the x-ray table. Electrical conduction paths between the two layers are used to monitor the patient's physiologic parameters, deliver therapeutic gasses or electrical power, or control other devices. In one embodiment, a capacitive electrocardiographic system is sandwiched between the two layers, where the leads are situated under the patient and a system for conducting the electrical signal to a detector passes between the layers of the table shield. Similar device sensors or therapeutic devices can be mounted into the space between the shield layers.

In another embodiment, the surface of the table shield is treated to retard the growth of infective agents such as bacteria (using silver impregnation, quanternary ammonium salts, or other agents). In another embodiment, an electrical heating element between the table shield layers can be activated, causing the surface temperature of the other table shield to rise to above 161 degrees Fahrenheit, thereby potentially providing a reduction in the number of infective agents.

The table shield may include vertically-oriented, curved slats or stays that are shaped to cause the drape to curve inwardly and under the x-ray table when hanging passively from the table. The extension of the drape inside the outline of the x-ray table is accomplished by providing a curve in the stays that bow the shield out from the table a small distance and then curve under the table for a shorter distance. This creates a center of gravity of the hanging shield such that the lower portion will passively hang under the table. The inward curve intersects the scatter radiation under the table and prevents radiation from exiting from beyond the outlines of the table, thereby providing more protection without requiring the drape to extend all the way to the operating room floor.

Another aspect of the table shield is that the flexible material is easily moved by the tube when the C-arm swings to oblique angles. Protection is maintained while the stiffening stays prevent the flexible material of the table shield from folding or sagging over the tube and interfering with the imaging beam. This will allow the physician to obtain unobstructed patient fluoroscopy images at various angles without interference from the shielding system. Moreover, the flexible nature of the shield will still provide personnel protection when the shield is pushed upward by the x-ray gantry.

In one aspect, the shielding system rests on the x-ray table, allowing it to move with the patient and provide scatter radiation shielding around the circumference of the patient from the pelvis to the head. This is of particular importance to personnel who must stand near the head or chest.

Other aspects of the table shield of the invention include stays that can be straight or they can consist of articulated components such that the stays passively flex, allowing the shield to bend around the x-ray tube housing but still hold the shielding out of the path of the primary x-ray beam. The stays can be permanently fixed to the flexible material or they can slip into a pre-sewn or formed track within the shield.

Physicians may need to bring the x-ray tube housing and gantry to a position where the beam is directed through the sagittal plane of the patient (often referred to as a "cross-table lateral view"). In this case, the table shield described would cover the x-ray beam. The flexible table shield described may be manually moved out of the way during rotation of the gantry into the cross-table lateral view, allowing it to drop back into a vertical position once the gantry reached the horizontal orientation and cleared the flexible table shield.

In another embodiment, one side of the table shield would be reversibly detachable, allowing the x-ray tube housing to rotate above the x-ray table. In another embodiment, the table shield would only cover a portion of the circumference of the x-ray table. For example, if no personnel were station on the patient's left side, that side of the shield could be omitted.

Flag Shield

Another aspect of the invention provides a transverse flag shield with an element that attaches the flag to the sled, the patient's mattress, the table the patient lies on, a free standing device or to a wall or ceiling mount. The attachment mechanism has one or more rigid arms connected at an angle, such that an arm(s) are horizontal and extend from the Attachment mechanism. Below one of the arms is a radiation absorbing material configured in such a way as to conform to the patient's body. Above the same or another arm is a radio-absorbing material that can be reversibly displaced. For example, an x-ray camera can be positioned such that it passively pushes away only a portion of the upper part of the shield obstructing the camera to allow the camera to be positioned for a particular x-ray view. This passively minimizes the gap in x-ray blockage.

One aspect of the invention provides a flag having elements to conform to patients' body habitus and other elements to flexibly and reversibly deform to accommodate other equipment in the environment of the operating room. Even though the upper unit of the flag shield is partially displaced, the lower functional unit is allowed to remain in place on the patient continuing to block radiation scatter from the patient's body while the upper unit bends away and conforms to the image intensifier. In addition, the flag shield can mate with the tray shield to seal the gap between the shields and prevent radiation leakage between the devices. In this way, the lower element of the flag shield conforms to the patient, the upper level of the shield conforms to the x-ray equipment movement, and the flag and table shield mate to each other, providing a complete blockage of x-radiation leakage.

The elements of the flag may have vertical supports throughout. The supports contain a hinges or a spring apparatus to allow the flag to bend in the vertical plane. This allows the flag to conform to other radiation absorbing material, such as a tray of the invention, allowing the flag to form a shell around the patient to continue blocking the radiation scatter. Because the flag has elastic properties, when the image intensifier moves away from an interfering position, the flag returns to its initial position, preventing gaps in the shielding where radiation may be emitted towards the HCW.

Another aspect provides a flag with asymmetric curves, which contour to a patient's body habitus, in the lower functional unit to maximize radiation protection to the HCW. This novel invention contrasts with current devices, which are pushed out of the way by the image intensifier or the HCW to prevent getting in the way of the HCW being able to work with catheters etc. The present invention, conversely, allows the lower portion of the flag to stay in place without moving away and also adds the ability of the upper functional unit to continue to offer radiation protection. This combination minimizes or eliminates the interference to the HCW work flow and allows them to continue their procedure uninterrupted.

The connection between the flag shield and tray shield may be mechanical interference fit, detents, magnetic attraction or other means.

Body Shields

In another embodiment, personnel scatter radiation exposure above the table is attenuated by attachment to the flexible table shield, or to the shield that covers the x-ray table, one or more radiation shields cover various body parts, but particularly the pelvis, chest and shoulder/neck areas.

In one embodiment, rigid or flexible stays within the attached body shields keep the shield in an expanded state while allowing the shield to conform to the body contour. In one embodiment, the stays allow the shield to be folded easily (such as by rolling the shield perpendicular to the stays) and in a further embodiment, magnets within the stays help maintain the shield in a folded position.

Since patient and procedure needs vary, the body shields can be reversibly detachable from the table shield using a variety of mechanisms, such as a zipper or hook and eyelet mechanism.

The body shields may be used instead of, or in addition to, the wing shields.

Wing Shield

Another aspect of the invention, used in conjunction, or independently of, a tray is one or more vertical shields that extend upwardly from the table to a variable height. The shields aid in preventing radiation exposure to the HCW resulting from oblique or horizontal beams coming from deflecting surfaces, such as the patient's bones, the bottom of the tray, or other equipment, or radiation traveling directly from the tube at oblique angles due to the tube being positioned at oblique angles to the patient.

The invention provides shields designed for placement at various locations relative to the patient. These shields move passively when pushed by the x-ray equipment and then return to their original position when the x-ray equipment moves away.

Side shields, or "wings" attached to the arm board or sled extend vertically along the side of the patient, creating a wall of a desirable height between the HCW and the patient. The wing shields can be displaced passively by x-ray equipment. In one embodiment, the wing shields are attached to the patient arm board using a spring hinge. The wing shield is pushed away from the patient when the x-ray system is rotated to a lateral position (such as 45 degrees right anterior oblique) and returns to its upright position when the x-ray equipment is moved to an anterior-posterior position.

The wing may have a number of shapes depending on the room and equipment. In one embodiment, the wing shield is curved from top to bottom, contains a clear window to observe the patient, and/or has deflector pieces that interact with the x-ray system to deflect the shield when the x-ray system approaches the wing shield from the headward or footward edges.

Workbench Shield Directly Above Patient

One aspect of the invention provides a tray assembly as an alternative to a DXAM drape over the patient. The tray placed over a portion of the patient forms a radiation blocking workbench used by the physician during the procedure. The tray is generally horizontal and may curve downward on the end facing the operator. The tray is positioned across the patient's body near the vascular access site so that catheters and other tools may rest on a level surface rather than on the arm or legs of the patient. The tray is composed of a radio-opaque material that blocks x-radiation. The radio-opaque material absorbs x-ray photons emitting from the patient while the patient is undergoing an x-ray imaging procedure. The curve of the tray blocks radiation emitting from the side or legs of the patient. The operator radiation exposure is therefore reduced.

The tray may be connected to an attachment apparatus that connects the device to a supporting structure (such as the mini-sled or a bed or x-ray table). The attachment apparatus is fastened to the sled, mattress or table that the patient lies on or to a side-rail attached to a supporting structure. A mechanism in the attachment apparatus allows the tray to rotate around the axis of the attachment apparatus, to flip up toward the attachment apparatus, and to tilt with one edge of the tray closer or farther away from the patient. The attachment mechanism itself can travel in a vertical up and down motion to move the tray above the patient and to lower the tray to the patient's body. This allows the tray to be positioned across and just above the patient easily, which allows the device to accommodate patients of different body shapes. It also allows for the tray to be removed up and out of the way quickly in case of emergency, and to allow for ease of patient transfer onto and off of the mattress.

Another aspect of the invention provides a tray that is of a laminar construction with one or more layers of radio-opaque material and one or more layers of material with minimal x-ray absorption (such as carbon fiber).

In another embodiment the tray is composed a clear x-ray absorbing material such as a clear plastic polymer with a high content of an x-ray absorbing material (such as boron, beryllium, barium).

In another embodiment, the tray has attachments that do not absorb x-rays, such as a piece that connects to the attachment apparatus and the tray.

In another embodiment, the tray has a forward edge that curves upward to more comfortably rest against the patients belly to further block radiation from the body. In addition, this edge can mate with the flag attachment, creating a radiation blocking seal between the two devices. The connection between the workbench shield and the flag shield can be passive or active (such as with magnets or using mechanical means).

In another embodiment, the flag shield and the workbench shield can be permanently fixed and function at a single shield.

In another embodiment, the tray is attached to a free standing device.

One embodiment of the tray has cut outs to facilitate access to parts of the body, such as the femoral artery and vein, while minimizing x-ray transmission. In addition, radio-opaque flaps or barriers attached to the access sites can be opened and closed to allow access when the x-ray is off. In addition, ridges may be used near the access site to block x-ray photons that are directed at the operator's position.

One aspect of the invention is a tray that has attachment devices to hold sterile surgical instruments, imaging devices, or supplies. These attachments allow the operator to have free hands for other tasks, such a puncturing an artery while the attachment holds an ultrasound probe to visualize the artery through the skin. In one embodiment, the attachments are connected to the tray underneath the sterile barrier or surgical drape and in another embodiment, the instruments are attached over a sterile barrier or surgical drape. These connections between the attachment and the tray may be mechanical (such as a clip under the drape) or magnetic (with the attachment containing a magnetic component that mates with a magnetic component within the tray under the drape).

In one aspect of the invention, the tray also has indentations that provide storage areas for surgical devices and supplies, such as needles, guidewire attachments, gauze, suture, and sterile fluids. In addition, the tray has spring clips and other attachment devices to hold catheters and wires emanating from the body. This stabilizes the positions of the catheters or wires and frees-up the operator's hands.

In one or more embodiments, a light may be attached to the tray illuminates the surgical area. The light may be controlled by a switch on the tray or by a remote device (such as a wireless device). The light can provide general lighting to the procedure area or a focused light on a particular area of interest. The lights are often dimmed in the x-ray imaging rooms and white light can interfere with the operators viewing of procedure monitors. In one embodiment, lights of different colors are used to provide lighting that optimizes the viewing of x-ray and vital sign monitors.

In another embodiment, the tray, which is positioned over the body, is used to assist in a procedure by placing force on the body. During some types of surgical procedures, pressure needs to be applied to the body, for example, to stop bleeding or compress a hematoma. This can be challenging when the bleeding occurs next to the surgical site. The operator needs to be manipulating catheters or surgical devices and cannot press on the body at the same time. An assistant's hands in the field obstruct the operator's hands. A tray is provided with a balloon or active device under the tray can be inflated or activated to produce pressure on the body. When a balloon is employed, the balloon can be inflated by an electric pump, a manual pump operated by an assistant outside the sterile field, a manual pump pumped through the drape by the operator. Alternatively, a simple broad foot can be extended mechanically (such as a ratchet mechanism) down from the lower surface or side of the tray and mechanically locked into place.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 is side elevation of an embodiment of a mini-sled of the invention;

FIG. 2 is a top plan view of an embodiment of a mini-sled of the invention;

FIG. 3 is a side elevation of an embodiment of a mini-sled and table shield of the invention;

FIG. 6 is an is a side elevation of an embodiment of a mini-sled and table shield of the invention;

FIG. 7 is a manufacturing step of an embodiment of a table shield of the invention;

FIG. 16a is a depiction of an embodiment of the tray being repositioned relative to a patient;

FIG. 16b is a depiction of an embodiment of the tray being repositioned relative to a patient;

FIG. 16c is a depiction of an embodiment of the tray being repositioned relative to a patient;

FIG. 16d is a depiction of an embodiment of the tray being repositioned relative to a patient;

FIG. 26 is a graph showing the data collected at the various data-gathering points diagrammed in FIG. 21; and FIG. 27 is a graph showing the data collected at the various data-gathering points diagrammed in FIG. 21.

DESCRIPTION OF EMBODIMENTS

Figure 4:
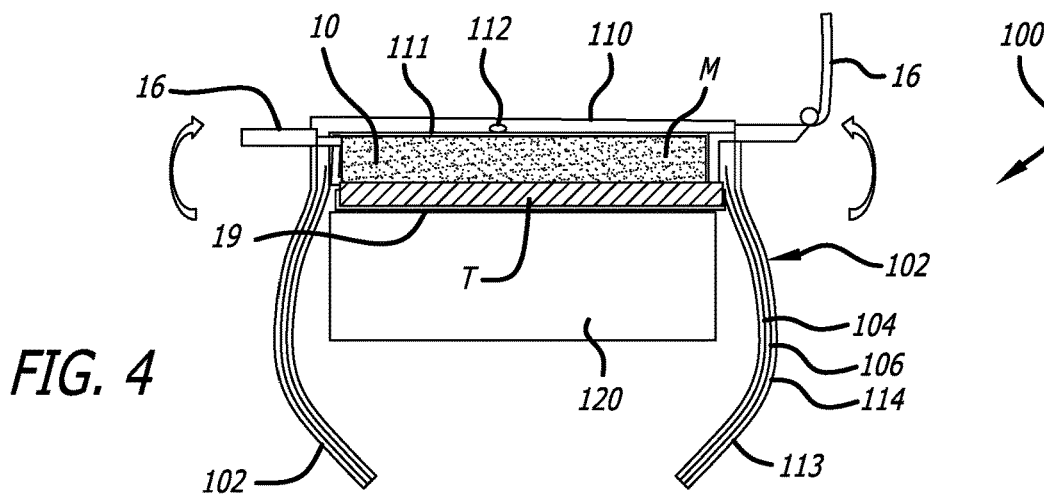
FIG. 4 is an end cutaway view of an embodiment of a mini-sled and table shield of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The system of the invention includes a suite of shields and accessories that provide protection and convenience to HCWs working in x-ray imaging environments. The suite generally includes several components that extend from, or are attachable to a sled (body length) or mini-sled (torso length) that carries a mattress and is attachable to an x-ray table. The sled does not have radiation protection properties but acts as a foundation for the radiation protection suite, though all of the components of the suite are not necessarily attached to the sled.

The radiation protection suite of the invention includes table shields, which extend below the table and protect the HCWs from the waist down. The suite also includes vertical flags that extend upwards and across the body of the patient. The suite further includes body shields, which extend upward from the sled and run along the sides of the patient. Wing shields are also included, which also extend upward along the sides of the patient. The wing shields are generally higher and more rigid than the body shields, providing more protection in high dosage areas. Finally, a tray is provided that extends horizontally across the body of the patient and provides both shielding as well as a work surface for the HCWs.

The various components of the system are now detailed, with reference being made to the Figures.

Sled/Mini-Sled

Referring now to FIGS. 1 and 2, an embodiment of a "mini-sled" 10 of the invention is provided. Generally, the sled 10 is a shallow, U-shaped frame that holds a mattress M on which the patient lies during the medical procedure. The sled 10 has a bottom 12 that lays on the x-ray table and two perpendicular sides 14, typically about 1-4 inches in height. The sled 10 can be the entire length of the mattress or shorter length. A pair of arm boards 16 are connected to the perpendicular sides 14 of the sled 10 with posts 18. A sheath 19 extends down under the sled 10 and is sized and shaped to receive a standard x-ray table T for securement thereto.

Table Shields

Turning now to FIGS. 3-9, there are shown embodiments of a table shield 100 of the invention. Table shield 100 prevents an HCW from radiation that is either reflected off of the various surfaces under the x-ray table, or directly from the x-ray tube. The table shield 100 is constructed of a flexible material such as vinyl fabric, that covers the patient procedure mat and table, where the sides of the material contain radiation blocking material. The surface of the table shield may be treated to retard the growth of infective agents such as bacteria (using silver impregnation, quanternary ammonium salts, or other agents). In another embodiment, an electrical heating element between the table shield layers can be activated, causing the surface temperature of the other table shield to rise to above 161 degrees Fahrenheit, thereby potentially providing a reduction in the number of infective agents.

The table shield 100 generally includes a side table shield 102 and a cross table shield 120. The side table shield 102 is positioned over the sled 10 passively (by gravity) or actively attached. The active attachment can be reversible (such as by a zipper or hook and eye mechanism) or non-reversible (such as with a bonding agent). The cross table shield 120 contains radiation blocking material and is attached beneath the table to the sled sheath 19. The cross table shield 120 extends across the width of the table at a point relative to the patient that is below the areas desired to be viewed on x-ray.

The side table shield 102 may include vertical slats or stays 104 that are curved or otherwise shaped to cause the shield to curve inwardly when hanging from the table, as seen in FIG. 4. The curved stays 104 reside in pockets 106 formed between the layers of the table shield 100.

FIG. 4 illustrates the construction of the table shield 100. The table shield generally includes a covering 110 that forms one continuous loop joined at seam 112, which is positioned on the bottom of the shield 100 and aligned midline on the sled 10. From the seam 112, the bottom of the covering 110, which is herein referred to as an under layer 111, extends across a foam insert or mattress M in the sled 10 and down the side of the table T. The under layer 111 continues to a lower extent at which point it folds over itself and around the inner materials of the shield 100 and becomes the outer layer 113 as it continues back up and across the table, directly under the patient. The outer layer 113 then repeats this pattern on the other side of the table T, extending down to a lower extent, where it folds under and once again becomes the under layer 111, which is routed back up until it reaches the seam 112.

Within the covering 110 is an x-ray blocking material 114 and several vertical stays 104, described above, which reside in pockets 106 and can be removed for storage. The stays 104 are shaped such that, when hanging from the table T, the offset geometric center of the stays 104 cause the lower edges of the side table shield 102 to curve inward.

Figure 5A:
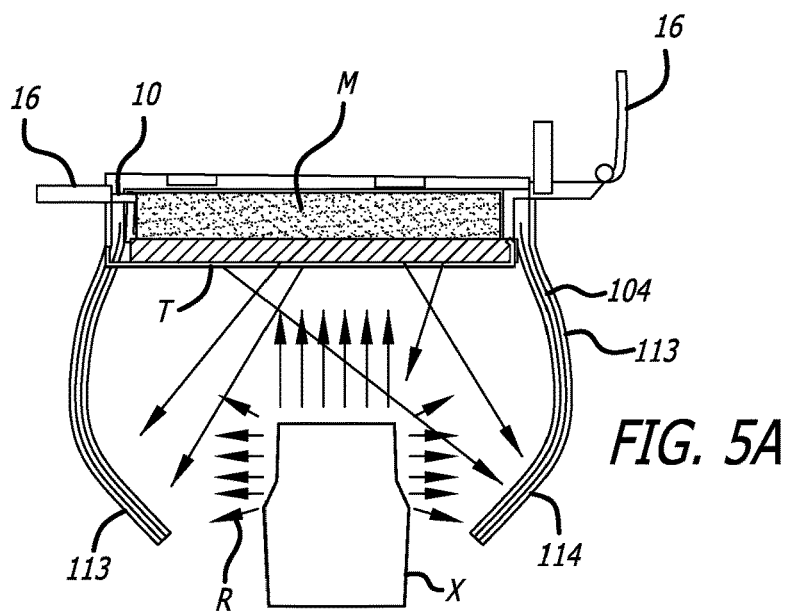
FIG. 5a is an end cutaway view of an embodiment of a mini-sled and table shield of the invention.
Figure 5B:
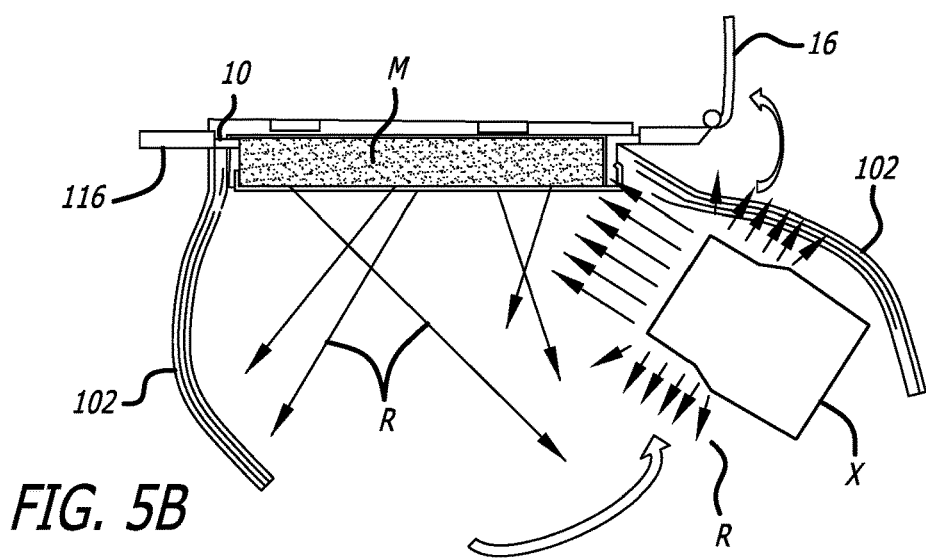
FIG. 5b is an end cutaway view of an embodiment of a mini-sled and table shield of the invention.

The importance of the inward curve of the stays 104 is best seen in FIGS. 5a and 5b. In FIG. 5a, the side table shields 102 hang naturally, curving inward at the bottom due to the shape of the stays 104. Shown is an x-ray tube X aimed directly up at the table T. The radiation, indicated by arrows R, emanates from the tube X but is blocked from hitting the feet of the operator by the inwardly curving side table shields 102.

In FIG. 5b, the x-ray tube X is swung to the side at an oblique angle. The closer side shield 102 is passively moved to the side by the tube X. The stays 104 maintain enough rigidity so that the shield does not fold or sag into the imaging path of the tube X.

In one embodiment, attachment points for arm boards, shields or other devices protrude from the sled through the table shield and attach to such devices. In the preferred embodiment, the arm boards rotate on the attachments to the sled, such that they can be flush to the sides of the sled in the down position, parallel to the x-ray table in the neutral position, or vertical above the sled in the up position. This allows stowage when transferring a patient off of the bed (down position), support of the patients arms during the procedure (neutral position), or clearance of the x-ray gantry when a lateral view is desired (up position). In addition, in the preferred embodiment, the arm boards pivot outward from the head-ward attachment, allowing the arm to abduct. This feature is important for radial arterial catheterization.

Similarly, the cross-table shield 120, which shares a similar construction to side table shield 102, may have vertical stays. No curvature is necessary for the cross-table shield 120. The shield 120 is pivotally connected to the sled sheath 19, which extends down from the sled 10. As seen in FIG. 6, the pivotal connection between the sheath 19 and the cross-table shield 120 allows the shield 120 to be moved passively by the tube X.

Figure 8:
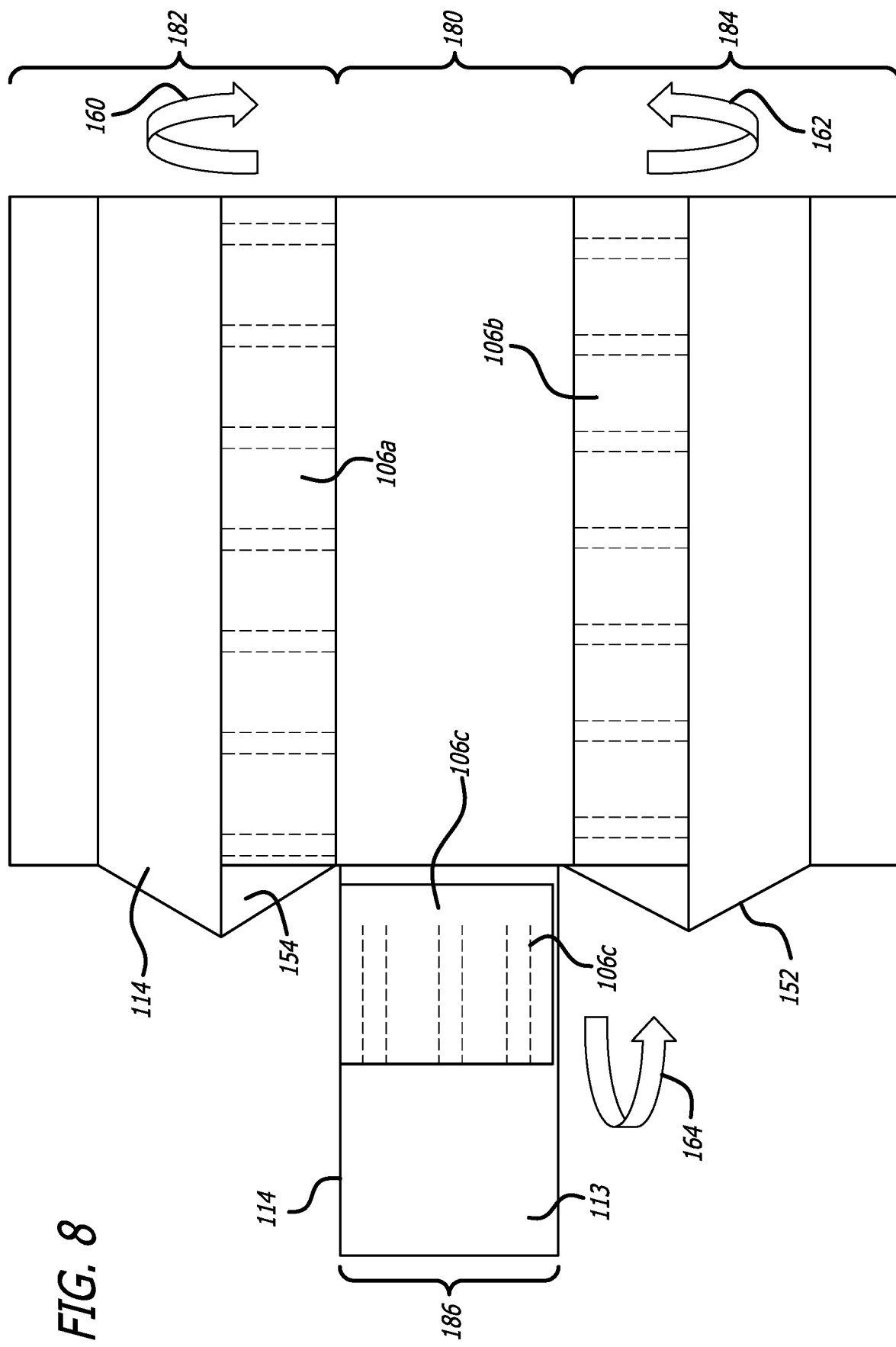
FIG. 8 is a manufacturing step of an embodiment of a table shield of the invention.
Figure 9:
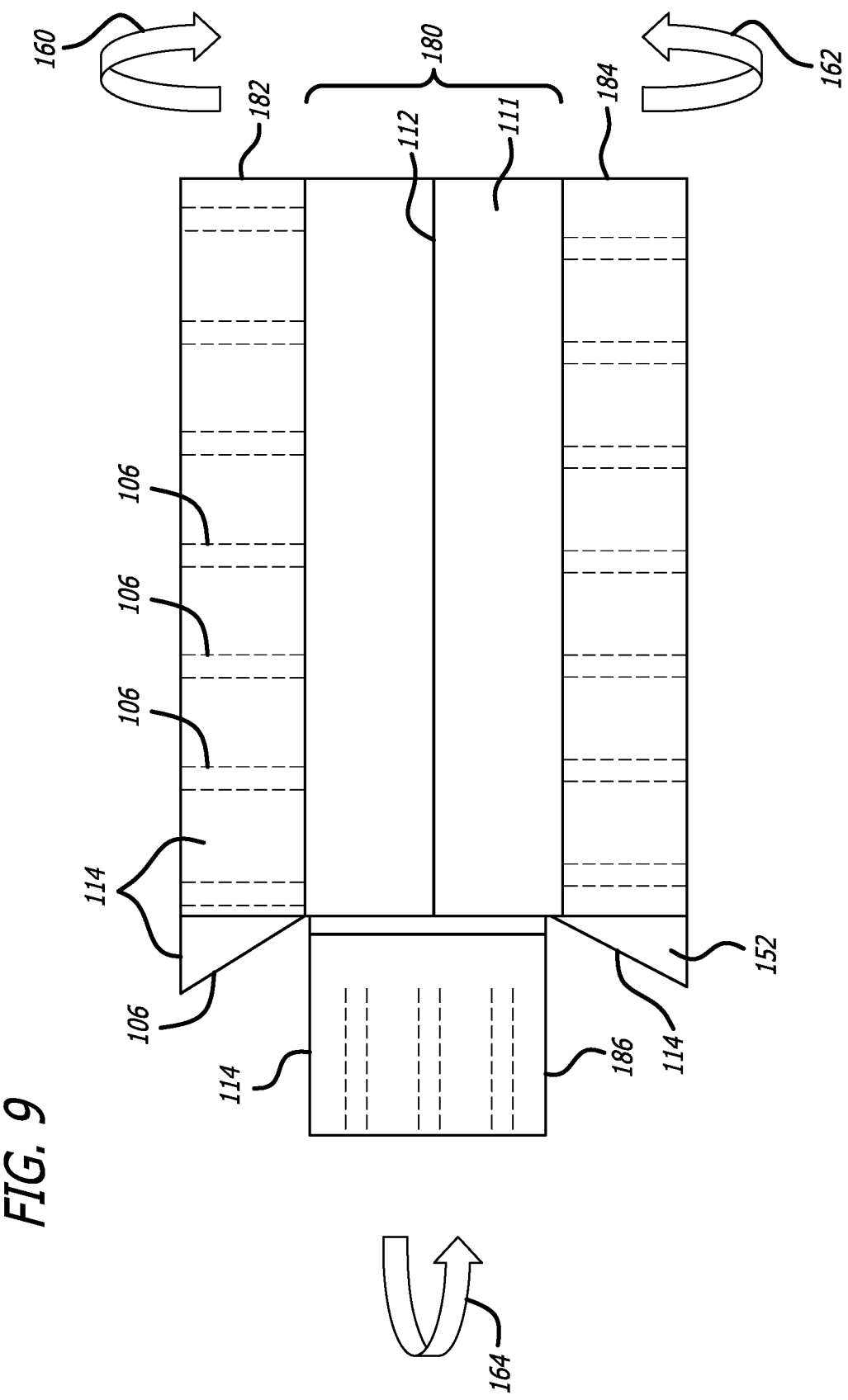
FIG. 9 is a manufacturing step of an embodiment of a table shield of the invention.

Referring now to FIGS. 7-9 a pattern 150 and steps for making one embodiment of the table shield 100 are provided. FIG. 7 provides the pattern 150 for the outer layer with dimensions given in centimeters. The pattern 150 can be broken up into four general sections, 180, 182, 184 and 186.

Section 180 is the center section that is sized to extend across the width of an x-ray table T. As will be seen, no radiation protection is necessary for section 180, as the purpose of section 180 is to provide an anchor from which the other sections hang.

Sections 182 and 184 will form the sides of the table shields 102. Section 186 will form a table shield 102 that will hang down vertically from the head of the patient. All of the shield sections 182, 184 and 186 contain radioabsorbant material as well as pockets 106 for stays. The pockets 106 of sections 182 and 184 will receive shaped stays while the pockets 106 of section 186 may receive vertical or shaped stays.

The locations of the pockets 106 shown in the figures are suggestions but have yielded good results. The sections 106a, b and c represent additional fabric sewn onto the vinyl covering 110 to form the pockets 106.

Triangular sections 152 and 154 form corner wraps that proved protection around the side edges of the shield 100, between sections 182 and 186, and between sections 184 and 186, when the side table shields 102 are hanging down.

FIG. 8 shows the addition of the radiation blocking material 114. Notably, no radiation blocking material is placed where on the horizontal surface of the resulting shield 100 as this would block the patient from being imaged.

Folds are then created at the intersections between the radiation blocking material 114 and the pocket sections 106a-c according to the folding arrows 160, 162 and 164. Folding results in the configuration shown in FIG. 9. Though the internal materials are illustrated in FIG. 9, one skilled in the art will realize that they are hidden by the layer 111 that results from folding and joining the edges to form seam 112.

Vertical "Flag" Shields

Figure 10:
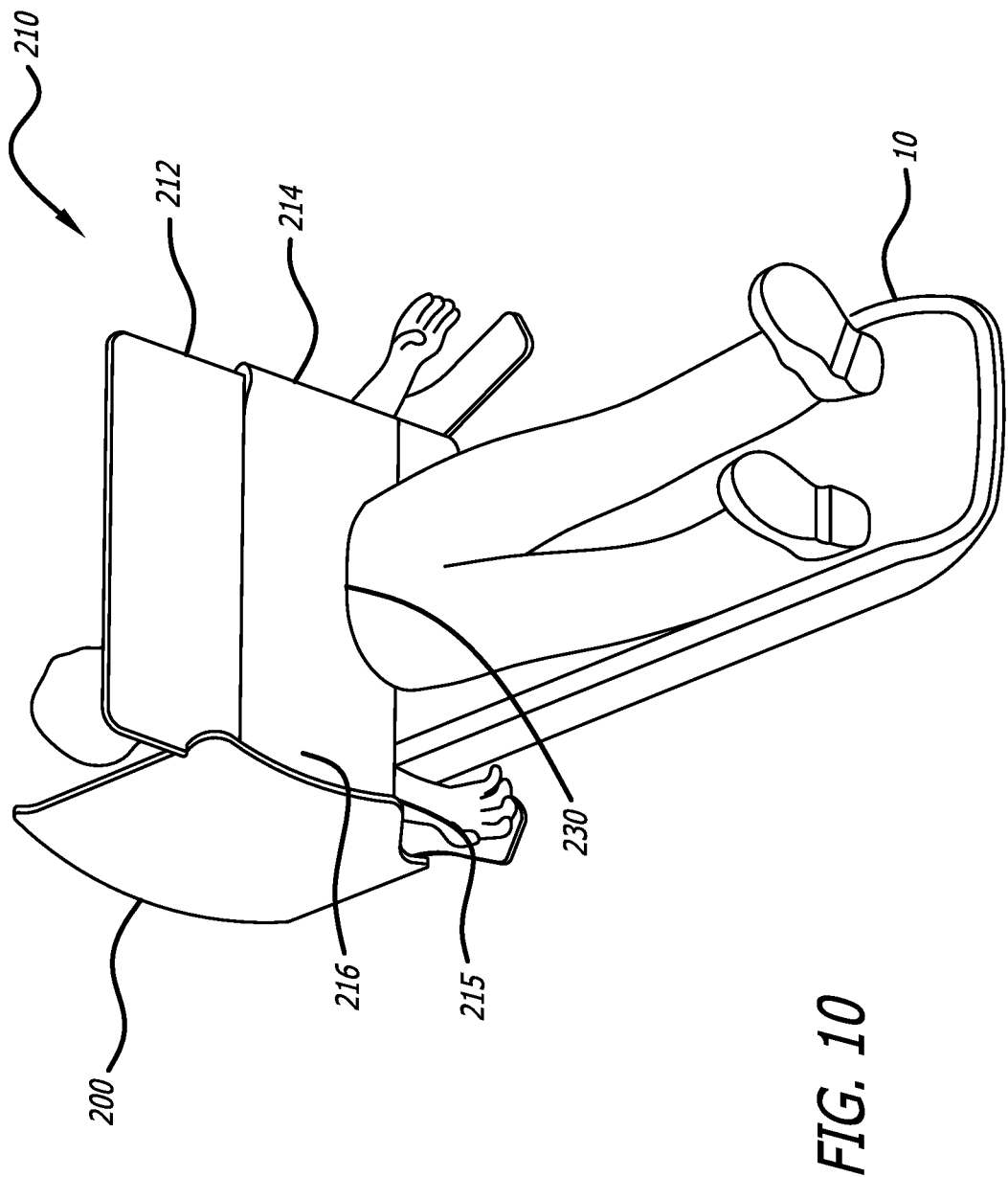
FIG. 10 is a perspective view of a patient on a table outfitted with an embodiment of a flag and an embodiment of a wing of the invention.
Figure 12:
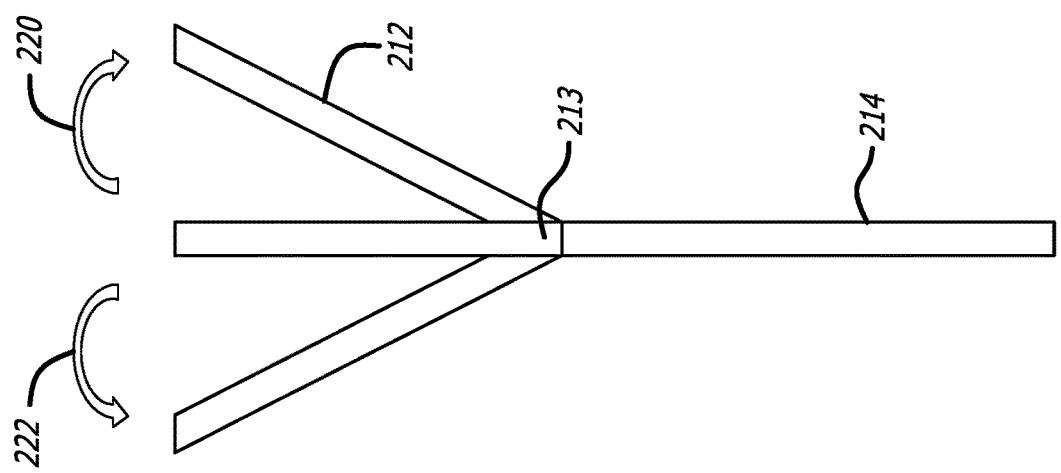
FIG. 12 is a side elevation of a flag of the invention.
Figure 11:
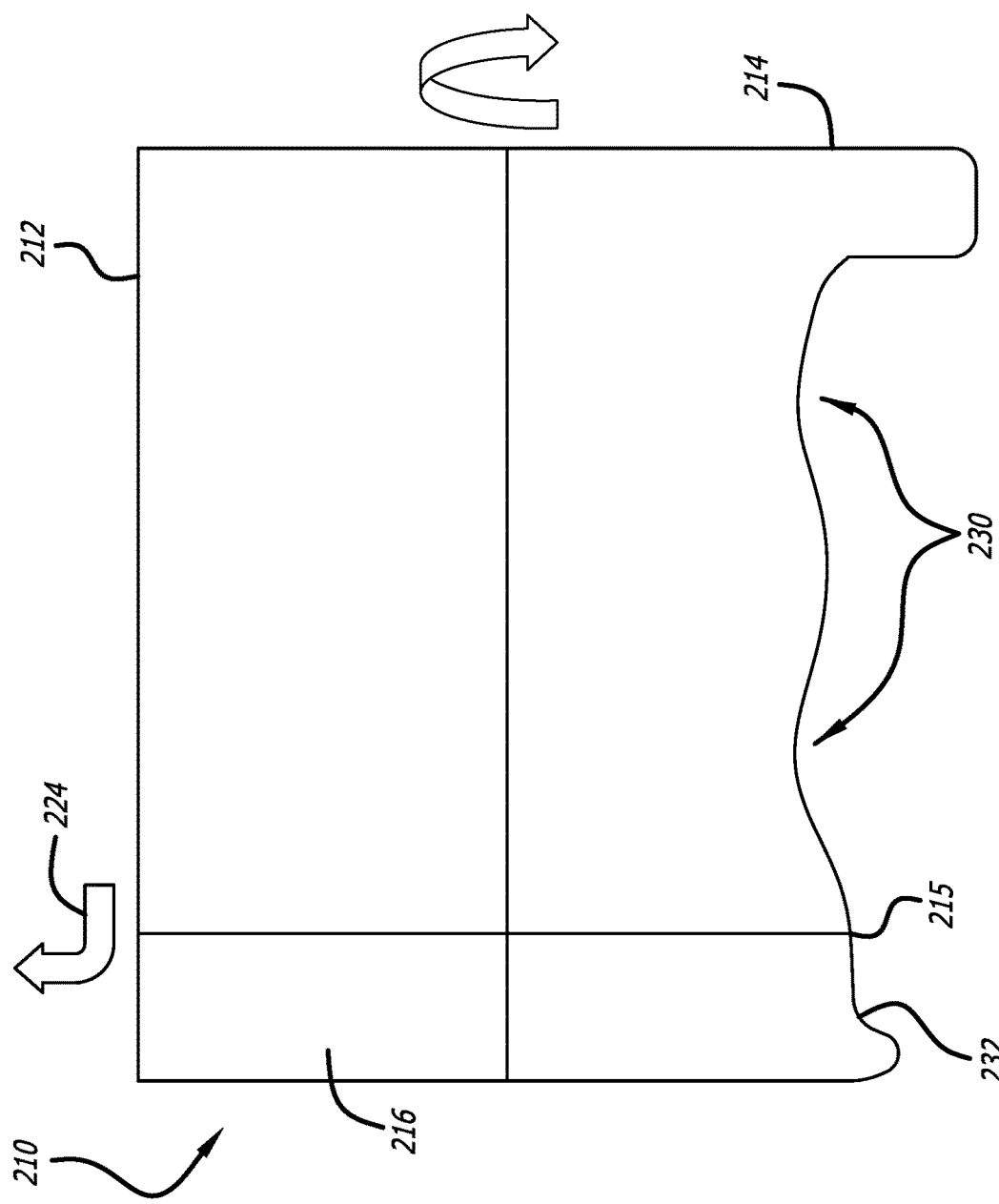
FIG. 11 is an elevation of a flag of the invention.

Turning now to FIGS. 10-12, there is shown a patient P shrouded by a wing 200 on the side and transversely by a flag 210. Transverse shield or flag 210 includes an upper unit 212, a lower unit 214 and a lateral unit 216. The upper functional unit 212 has a degree of internal flexibility/elasticity and has a horizontal articulation 213 with the lower functional unit 214, as best shown in FIG. 12 in which arrows 220 and 222 show the articulating movement of upper unit 212 relative to lower unit 214. The flag 210 also has vertical articulation 215 with the lateral functional unit 216 as indicated by arrow 224.

This articulation 213, 215 allows the upper unit 212 to freely move on a horizontal axis as well as have some elastic stretch when the equipment in the room such as an image intensifier pushes it to enable optimal imaging conditions. This the lower functional unit 214 is thus able to remain in place on the patient continuing to block radiation scatter from the patient's body while the upper unit 212 bends away and conforms to an image intensifier, for example. In addition, the flag 210 may have vertical supports throughout. The supports may contain a hinge or spring apparatus to allow the flag to bend in the vertical plane so that the flag 210 is able to conform to other radiation absorbing material, such as the wing 200, allowing the flag 210 continues to form a shell around the patient to continue blocking the radiation scatter. Because the flag 210 has elastic properties, when the image intensifier moves away from an interfering position, the flag 210 returns to its initial position, preventing gaps in the shielding where radiation may be emitted towards the HCW.

As best seen in FIG. 11, the lower unit 214 includes bottom curves 230 that contour to a patient's body habitus in order to maximize radiation protection to the HCW. Similarly, the bottom of the lateral unit 216 includes a cutout 232 to contour to a patient's forearm.

The upper, lower and lateral units 212, 214, 216 may be composed of multiple vertical strips of overlapping material to provide greater flexibility with positioning the barrier around objects. Additionally, the radioabsorbent barriers on the top or bottom of the flag can be composed of multiple overlapping material, such that an object displacing one piece of material would not displace the adjacent section. This would improve radiation protection.

The flag units 212, 214, 216 can be constructed of radioabsorbent fully or partially transparent material or could have a radioabsorbent clear window (not shown) in portions to allow for optimal patient visualization. The flag 210 also can hold a patient instruction and or entertainment window where a screen could be placed.

The flag 210 may be attached to the attachment mechanism 412 along with the tray 420. Alternatively, the flag 210 may be anchored to the mattress or patient table, to a separate free-standing mechanism, or to a wall or ceiling mount, with features that allow for rapid stowage. Like the tray 420, the flag 210 preferably has at least two, and more preferably three or more degrees of freedom.

Vertical "Wing" Shields

The wing 200, shown in FIG. 10, may be rigid or flexible and is a radioabsorbent wall that extends vertically along the side of the patient, and is height-adjustable to provide a desired level of protection between the HCW and the patient. Wing shields 200 are designed for placement at various locations relative to the patient.

The wing shields 200 may be attached to the arm board or sled, and extend vertically along the side of the patient, creating a wall of a desirable height between the HCW and the patient. The wing shields can be displaced passively by x-ray equipment. In one embodiment, the wing shields are attached to the patient arm board using a spring hinge. The wing shield is pushed away from the patient when the x-ray system is rotated to a lateral position (such as 45 degrees right anterior oblique) and returns to its upright position when the x-ray equipment is moved to an anterior-posterior position.

The wing may have a number of shapes depending on the room and equipment. In one embodiment, the wing shield is curved from top to bottom, contains a clear window to observe the patient, and/or has deflector pieces that deflect the shield when the x-ray system approaches the wing shield from the headward or footward edges.

Attachable Body Shields

Figure 13:
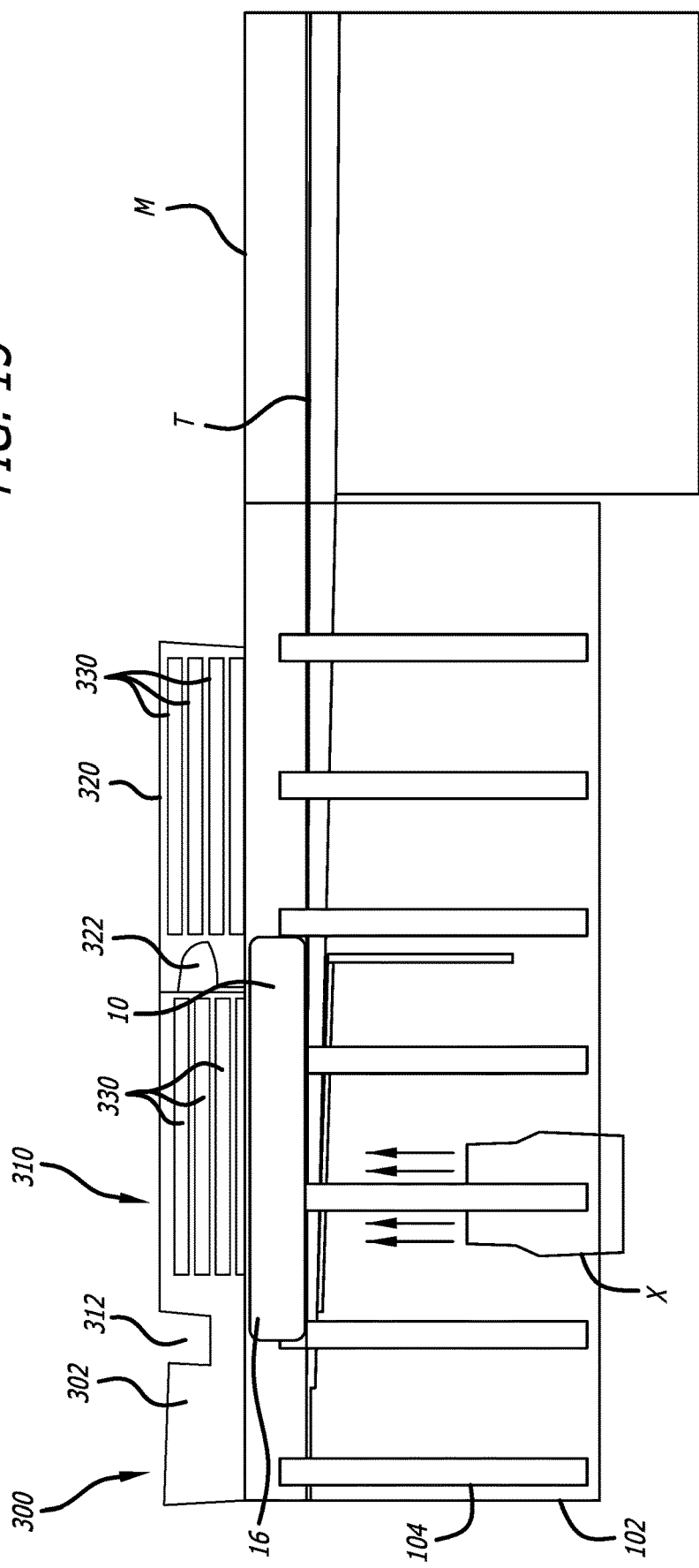
FIG. 13 is a side elevation of an embodiment of a body shield installed on a mini-sled of the invention.
Figure 14:
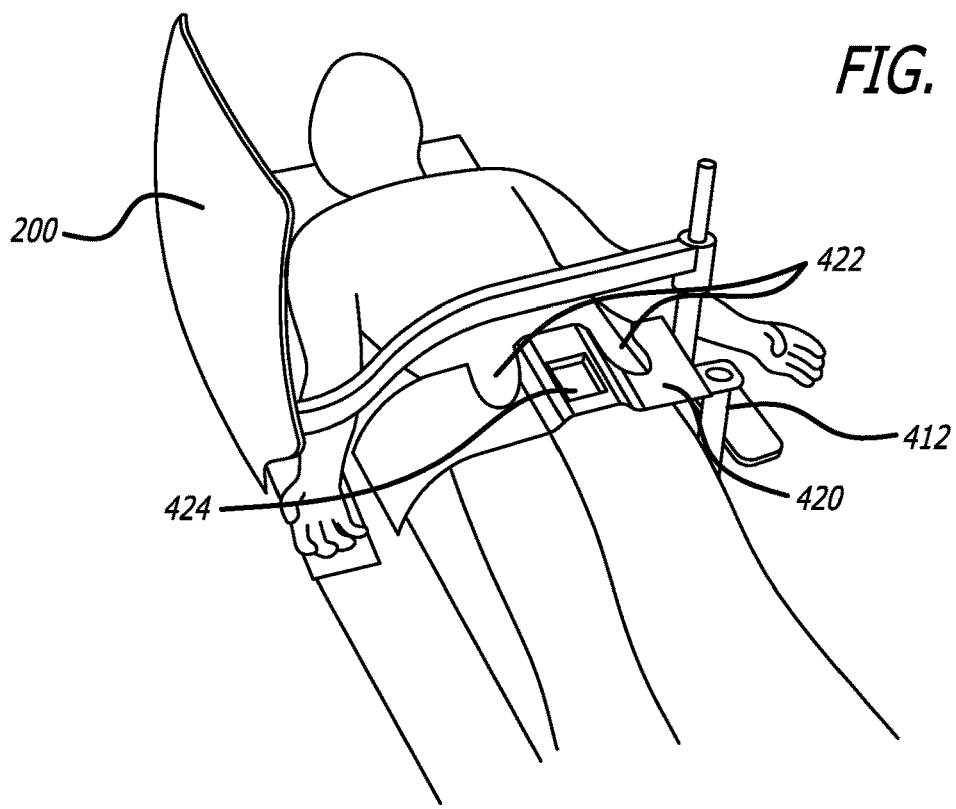
FIG. 14 is a perspective view of an embodiment of a tray and an embodiment of a wing of the present invention.

Referring now to FIG. 13 personnel scatter radiation exposure above the table is attenuated by attaching one or more flexible body shields 300 to the sled 10. to the flexible table shield, or to the shield that covers the x-ray table, one or more radiation shields cover various body parts, but particularly the pelvis, chest and shoulder/neck areas.

In FIG. 13, there are shown three body shields 300—a shoulder and head shield 302, a chest and abdomen shield 310, and a pelvic and leg shield 320. The shoulder and head shield 302 extends from an edge of the sled 10 to an area approximating the chin of the patient where it is joined by the chest and abdomen shield 310. One or both of the shields 302 and 310 join to form a neck cutout 312, which provides easy access to the neck of the patient P.

The chest and abdomen shield 310 extends to about waist level where it is joined by the pelvic and leg shield 320. The shield 320 has femoral artery cutouts 202 to align with the cutouts of the tray, if present, providing access to the femoral arteries.

Some or all of the shields 300 may have horizontally aligned stays 330 that are constructed and arranged, with magnets for example, to maintain a stacked configuration, if desired, or to maintain a folded configuration, if desired. Thus, the height of the body shields 300 can be adjusted by simply folding the shields over at a desired location between stays 330.

In one embodiment, rigid or flexible stays 330 keep the shield in an expanded state while allowing the shield to conform to the body contour. Since patient and procedure needs vary, the body shields can be reversibly detachable from the table shield using a variety of mechanisms, such as a zipper or hook and eyelet mechanism.

Radioabsorbent Tray

FIGS. 14-20 show a tray 420 of the invention. The tray 420 is a generally horizontal tray that, in use, is positioned above the patient and provides a working surface for the physician while shielding the physician from radiation. The tray 420 may have cutouts 422 for accessing the femoral arteries of the patient. This obviates the need to move the tray when using a femoral navigation approach.

Figure 15:
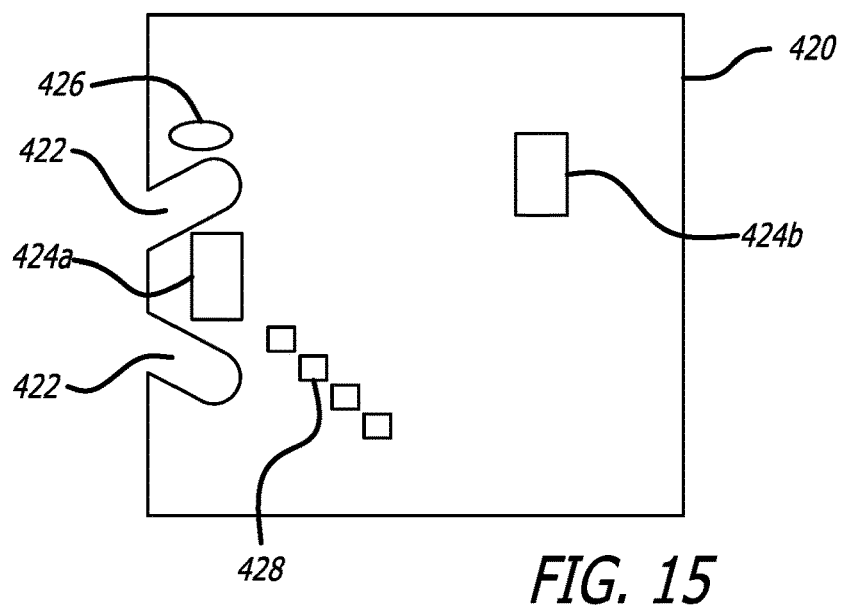
FIG. 15 is a plan view of an embodiment of a tray of the invention.

The tray 420 may also include various features for holding tools securely, providing convenient access for the physician. For example, the tray 420 of FIG. 14 includes a well 424, which is a simple recess for securely containing tools. FIG. 15 shows an embodiment of tray 420 having several tool accommodations. In addition to providing two wells 424, one of which (424*a*) is used to hold needles and angioplasty wire knobs, and the other of which (424*b*) is used to hold gauze in a sterile saline solution, the tray 420 of FIG. 15 includes a light 426 for illuminating the tools, reducing eyestrain for the HCW and improving safety. Also shown are one or more clips 428, provided for attaching the catheters or wires that may be attached or inserted into the patient.

The tray 420 is positioned over the patient with an attachment mechanism 412, such as a swing arm or boom. The attachment mechanism 412 provides at least two, preferably three or four degrees of freedom to the tray position, including adjustable height above the patient, horizontal rotation, horizontal translation, and vertical rotation or tilt. FIGS. 16*a-d* depict the adjustability provided by the attachment mechanism 412.

FIG. 16*a* shows the relative positions of the tray 420, the operator O, and the patient P. The tray 420 is shown with femoral cutouts 422. Also shown is an arrows 430, indicating the ability of the tray 420 to be translated horizontally in the direction of the arrows 430.

FIG. 16*b* shows the tray 420 rotated horizontally around a mast 414 of the attachment mechanism. Arrow 432 is provided to show the directions of rotation made available by the rotational connection of the tray 420 to the mast 414.

FIG. 16*c* provides a side elevation of the tray 420 in a horizontal orientation. FIG. 16*d* shows the tray 420 being tilted in the direction of arrow 434.

Figure 17:
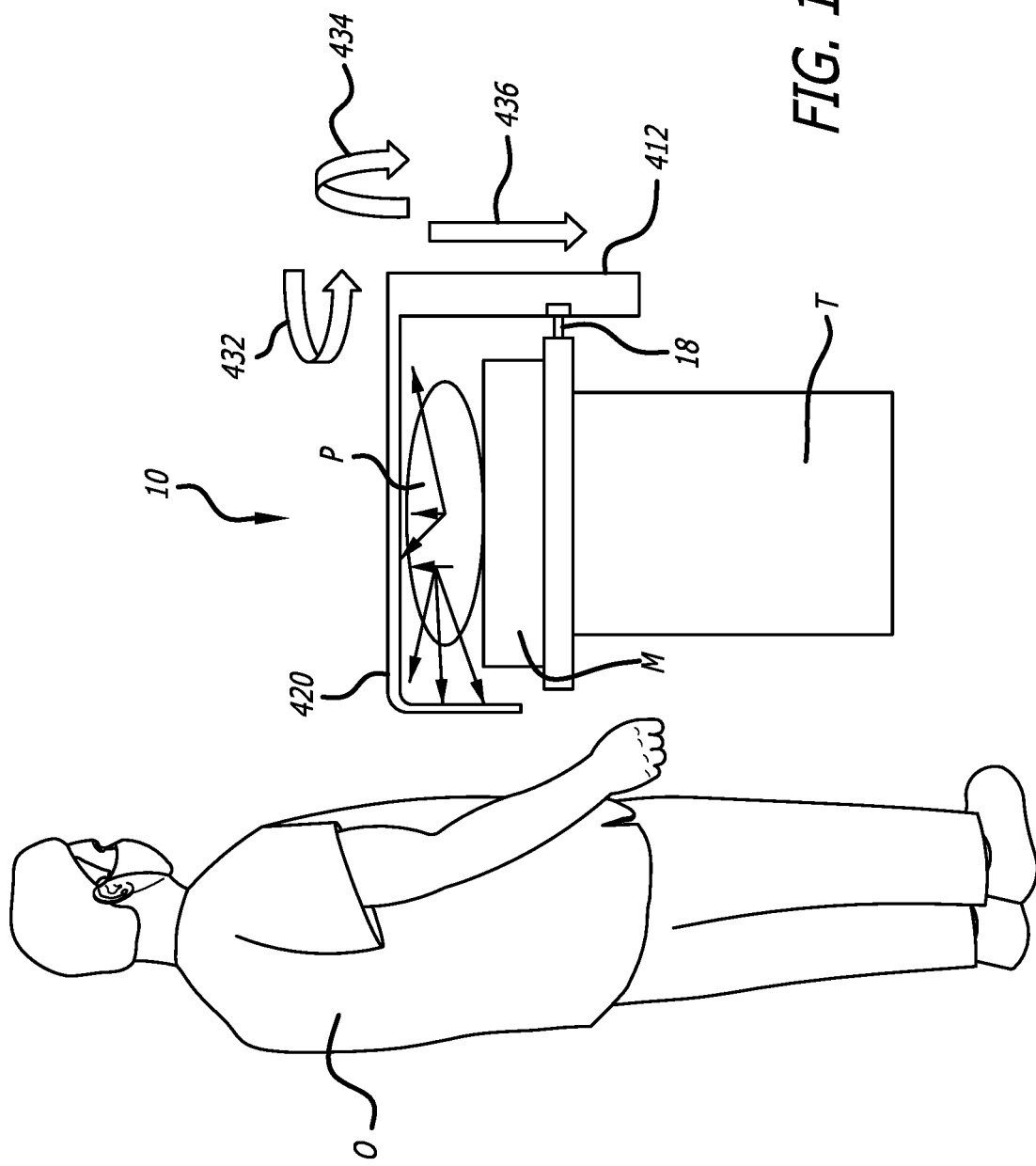
FIG. 17 is an end view of an embodiment of a tray of the invention showing relationship to a patient, mattress, table and operator.

FIG. 17 shows an end elevation of the tray 420 placed over a patient P lying on a mattress M. An operator O is attending to the patient P. Three arrows, 432, 434, and 436 are shown to indicate the degrees of freedom for horizontal rotation, tilt, and vertical adjustment, respectively.

Figure 18:
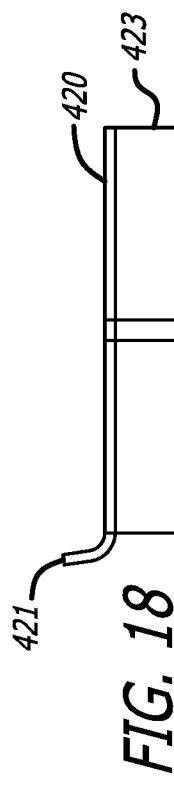
FIG. 18 is a side elevation of an embodiment of a tray of the invention.

FIG. 18 is a side elevation of a tray 420 showing that the tray 420 can be described as having two shielding components, a belly shield 421 and a side shield 423. Referring back to FIG. 17, the benefits of the belly shield 421 and side shield 423 are highlighted using radiation arrows R. The radiation arrows R emanate from the patient P but are blocked and absorbed both above, and to the side of, the patient P, thereby protecting operator O.

Figure 19A:
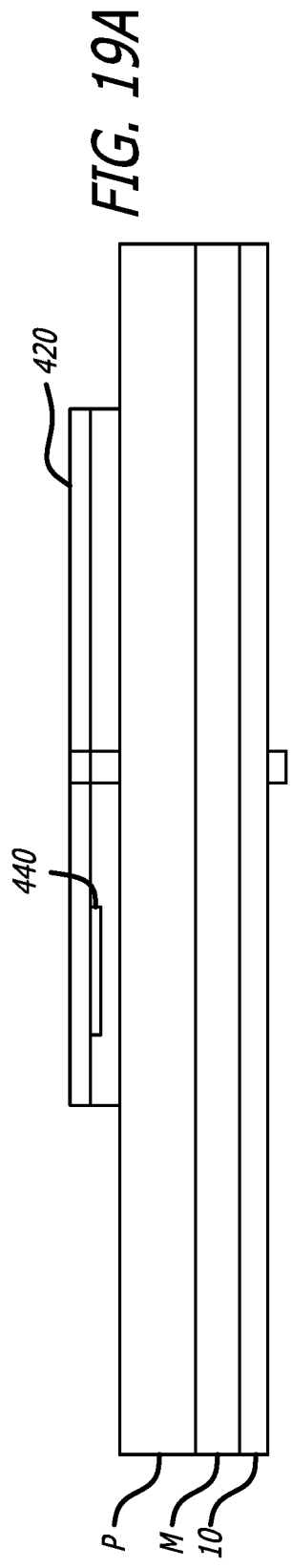
FIG. 19a is a side elevation of an embodiment of a tray having a compression mechanism of the invention.
Figure 19B:
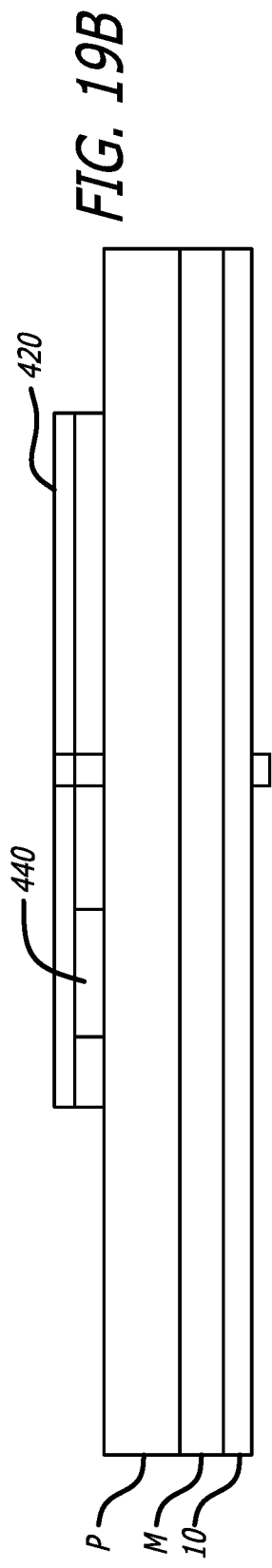
FIG. 19b is a side elevation of an embodiment of a tray having a compression mechanism of the invention.

It is not uncommon for the need to arise to put gentle pressure on the patient for various reasons. Pressing down on the patient during imaging necessarily exposes the HCW to even higher doses of radiation due to close proximity to the patient and also positioning him or herself above the patient to apply the pressure. FIGS. 19*a* and 19*b* show an embodiment of a tray 420 with a compression device 440 in the form of a balloon. The balloon 440 in FIG. 19*a* is shown as deflated and thus not applying pressure to the patient P. The balloon 440 in FIG. 19*b* is shown as inflated and thus applying pressure to the patient P. The rigidity of the tray 420 and the ability of the attachment mechanism to lock the position of the tray in place, provides a stationary force against which the balloon can act to apply pressure to the patient.

Figure 20:
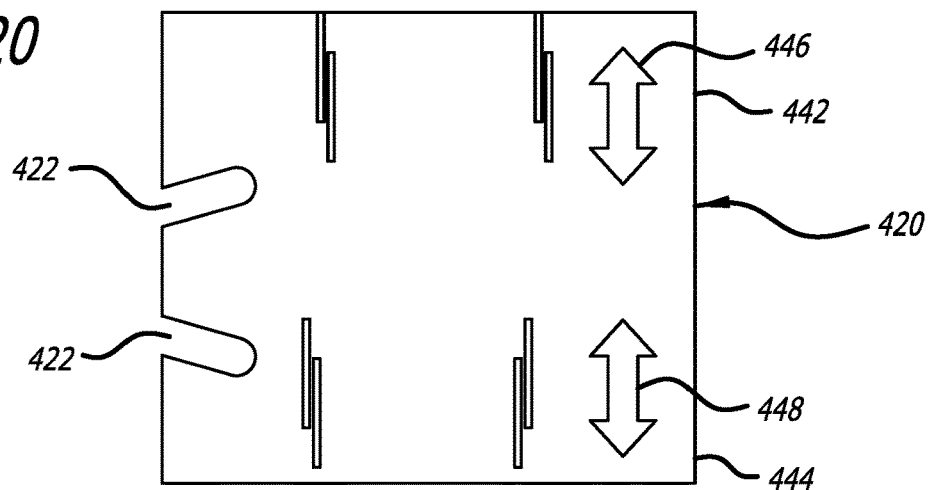
FIG. 20 is a top plan view of an embodiment of a tray of the invention having an adjustable width.

FIG. 20 shows a plan view of a tray 420 that has adjustable sides 442 and 444. The sides 442 and 444 have a sliding connection to the rest of the tray 420 such that the width of the belly shield 421 may be adjusted to accommodate different patient sizes. The adjustability of the sides 442 and 444 is depicted by arrows 446 and 448, respectively.

Data

An experiment was conducted to test the efficacy of the system of the present invention. A standard anthropomorphic X-ray phantom was acquired from the US Department of Energy and placed on the table of a Toshiba® Infinix® C-arm radiographic system. The settings were as follows:

15 fr/sec fluoroscopy
70 keV tube voltage
SID 100 cm
103-106 mA current

Figure 21:
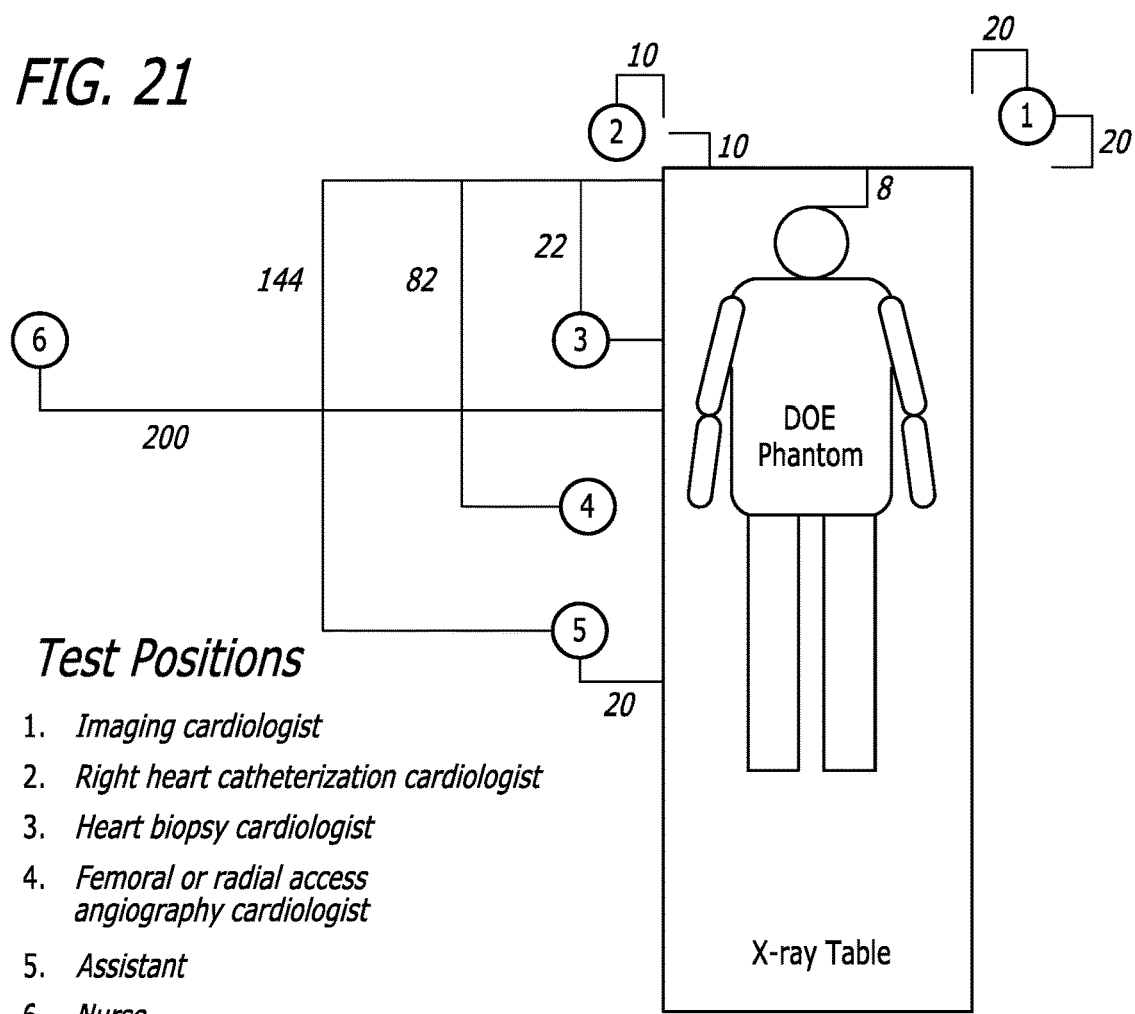
FIG. 21 is a diagram of an experiment conducted to determine the effectiveness of the various embodiments of the invention.
Figure 22:
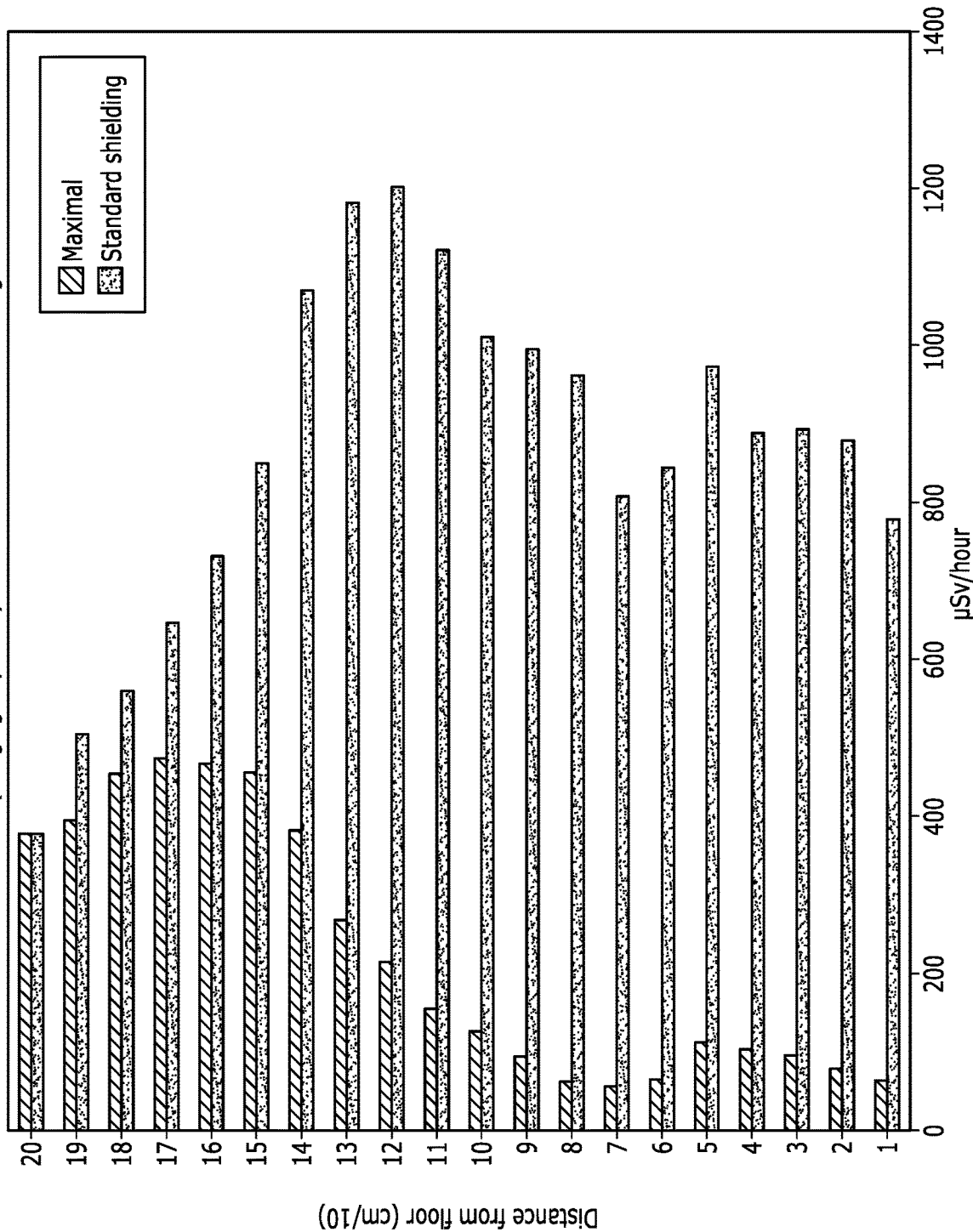
FIG. 22 is a graph showing the data collected at the various data-gathering points diagrammed in FIG. 21.
Figure 23:
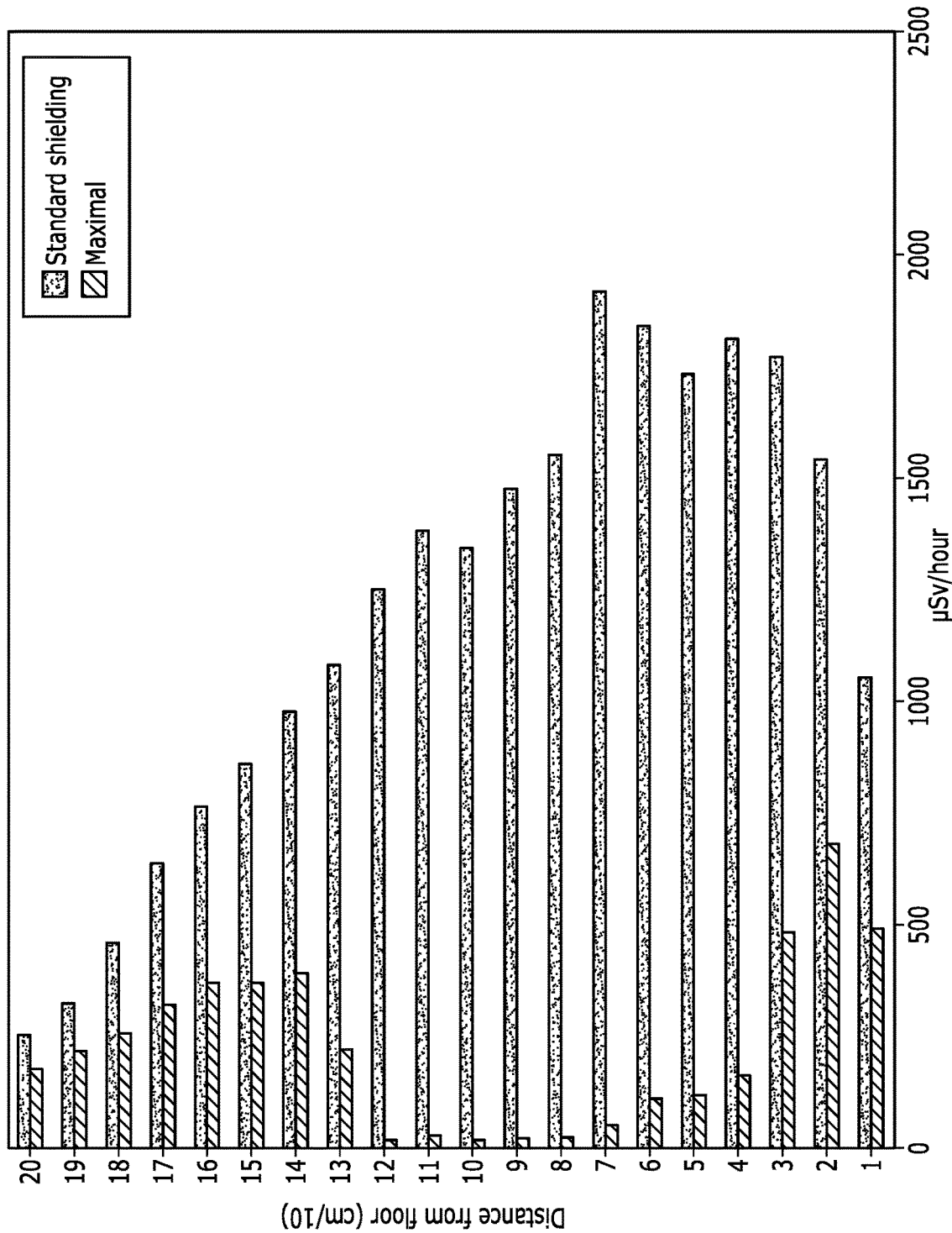
FIG. 23 is a graph showing the data collected at the various data-gathering points diagrammed in FIG. 21.
Figure 24:
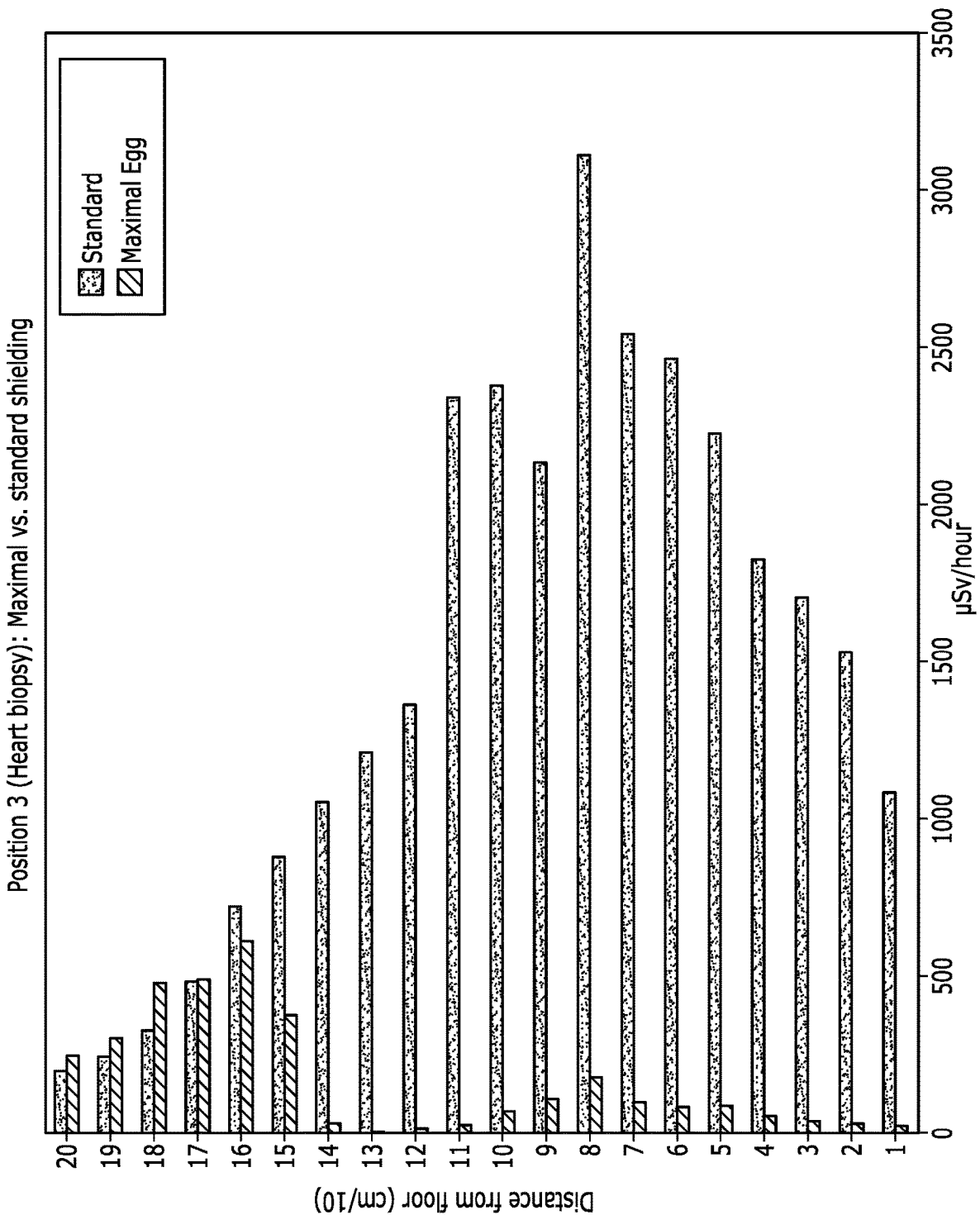
FIG. 24 is a graph showing the data collected at the various data-gathering points diagrammed in FIG. 21.
Figure 25:
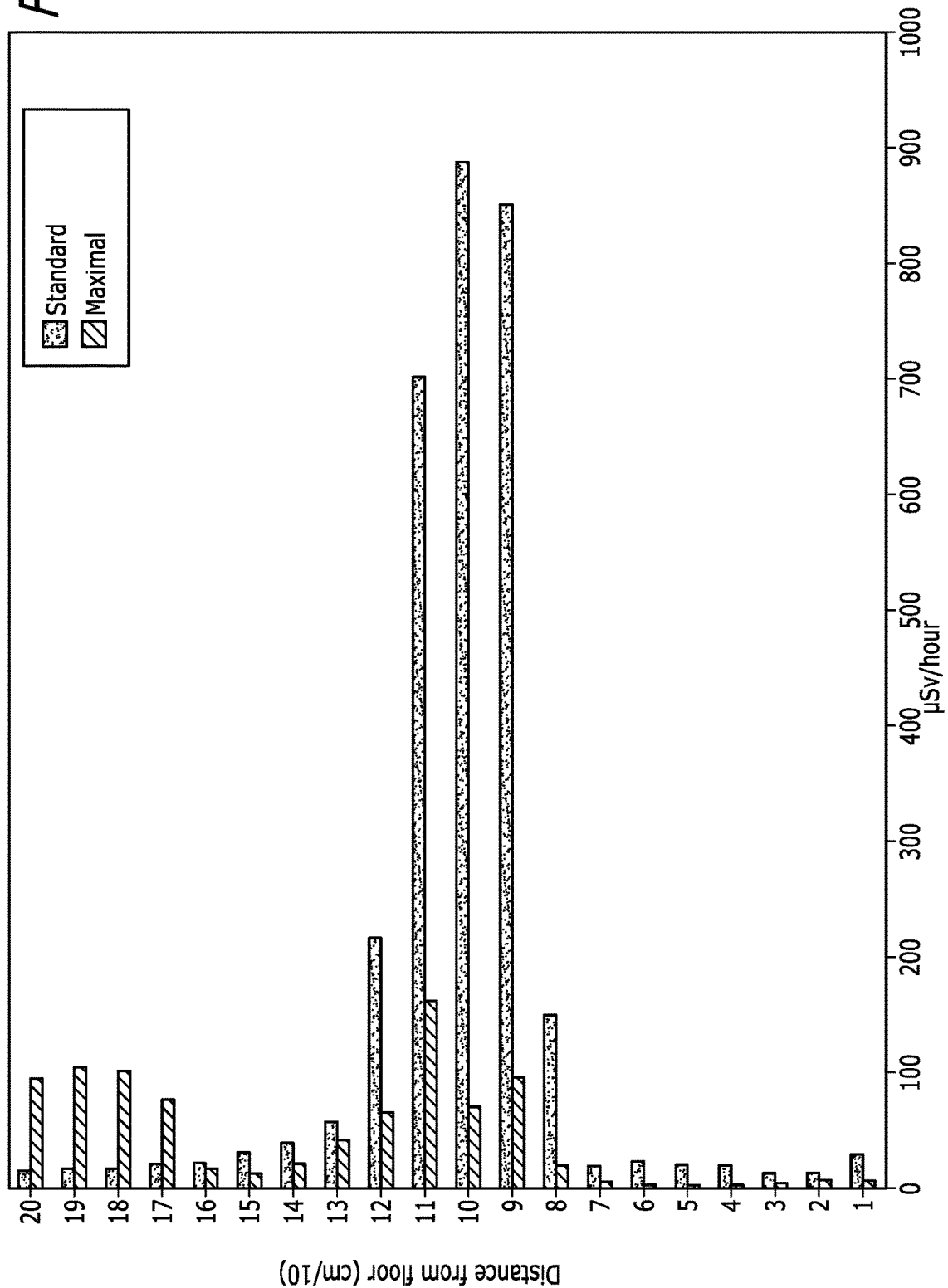
FIG. 25 is a graph showing the data collected at the various data-gathering points diagrammed in FIG. 21.

Scatter radiation was measured, using a Fluke® Biomedical X2 Sensor System, at various locations, and at various heights, throughout the room, according to the map provided in FIG. 21. FIG. 21 shows that 6 locations were identified as corresponding to locations were HCWs would typically stand as follows:

Position 1—Imaging Cardiologist
Position 2—Right Heart Catheterization Cardiologist
Position 3—Heart Biopsy Cardiologist
Position 4—Femoral or Radial Access Angiography Cardiologist
Position 5—Assistant
Position 6—Nurse The graphs shown in FIGS. 22-27 each correspond to one of the positions 1-6 of FIG. 21. Measurements were taken at several heights, beginning at 1 cm from the floor and extending up to $20c$ m at 1 cm intervals. Data was gathered for both a table using standard shielding as well as using the shielding of the present invention (represented in the table as "Maximal"). The results show a dramatic decrease in exposure at all six of the positions measured.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A radioabsorbent tray, comprising:
a working surface configured to shield a physician from radiation; and
an attachment mechanism for attaching the working surface to a medical table or bed; and,
wherein the attachment mechanism is configured to adjust the working surface with respect to the medical table or bed.

2. The radioabsorbent tray of claim 1, wherein the attachment mechanism is configured to adjust a height of the working surface.

3. The radioabsorbent tray for of claim 1, wherein the attachment mechanism is configured to adjust a horizontal rotation of the working surface.

4. The radioabsorbent tray of claim 1, wherein the attachment mechanism is configured to adjust a horizontal translation of the working surface.

5. The radioabsorbent tray of claim 1, wherein the attachment mechanism is configured to adjust a vertical rotation or tilt of the working surface.

6. The radioabsorbent tray of claim 1, wherein the attachment mechanism is configured to adjust a height of the working surface, a horizontal rotation of the working surface, a horizontal translation of the working surface, and a vertical rotation or tilt of the working surface.

7. The radioabsorbent tray of claim 1, wherein the working surface includes one or more cutouts for accessing a femoral artery of a patient.

8. The radioabsorbent tray of claim 1, wherein the working surface includes a well for securing containing one or more tools.

9. The radioabsorbent tray of claim 1, wherein the working surface includes a first well and a second well, the first well being configured to hold needles and the second well being configured to hold gauze in a sterile saline solution.

10. The radioabsorbent tray of claim 1, wherein the attachment mechanism is a swing arm or boom.

11. The radioabsorbent tray of claim 1, wherein the attachment mechanism includes a mast, and wherein the working surface is configured to be rotated horizontally around the mast.

12. The radioabsorbent tray of claim 1, further comprising a belly shield attached to the working surface.

13. The radioabsorbent tray of claim 1, further comprising a side shield attached to the working surface.

14. The radioabsorbent tray of claim 1, further comprising a belly shield and a side shield attached to the working surface.

15. The radioabsorbent tray of claim 1, further comprising a compression device attached to a lower surface of the working surface.

16. The radioabsorbent tray of claim 15, wherein the compression device is a balloon.

17. A medical table, comprising:
a horizontal bed for receiving a patient;
an attachment mechanism attached to the horizontal bed; and
a working surface attached to the attachment mechanism; and,
wherein the attachment mechanism is configured to adjust the working surface with respect to the horizontal bed.

18. The medical table of claim 17, wherein the attachment mechanism is configured to adjust a height of the working surface, a horizontal rotation of the working surface, a horizontal translation of the working surface, and a vertical rotation or tilt of the working surface.

19. The medical table of claim 17, wherein the attachment mechanism is a swing arm or boom.

20. The medical table of claim 17, further comprising a belly shield and a side shield attached to the working surface.

* * * * *